United States Patent [19]

Oku et al.

[11] Patent Number: 5,624,931
[45] Date of Patent: Apr. 29, 1997

[54] PYRAZOLE DERIVATIVES

[75] Inventors: Teruo Oku, Tsukuba; Yoshio Kawai, Ushiku; Hiroshi Marusawa, Yokohama; Hitoshi Yamazaki; Yoshito Abe, both of Tsukuba, all of Japan

[73] Assignee: Fujisawa Pharmaceutical Co., Ltd., Osaka, Japan

[21] Appl. No.: 471,175

[22] Filed: Jun. 6, 1995

Related U.S. Application Data

[62] Division of Ser. No. 269,520, Jul. 1, 1994, Pat. No. 5,478,827, which is a division of Ser. No. 931,093, Aug. 17, 1992, Pat. No. 5,356,897.

[30] Foreign Application Priority Data

Sep. 9, 1991 [GB] United Kingdom ............... 9119267
Mar. 2, 1992 [GB] United Kingdom ............... 9204464

[51] Int. Cl.$^6$ ................. A61K 31/505; C07D 487/04
[52] U.S. Cl. ..................... 514/258; 544/263; 544/281
[58] Field of Search ........................ 544/263, 281; 514/258

[56] References Cited

U.S. PATENT DOCUMENTS 5,356,897 10/1994 Oku et al. .

*Primary Examiner*—Yogendra N. Gupta
*Attorney, Agent, or Firm*—Oblon, Spivak, McClelland, Maier & Neustadt, P.C.

[57] ABSTRACT

Pyrazole derivatives useful for inhibiting the production of Interleukin-1 (IL-1) and tumor necrosis factor (TNF) and the like, which can be represented by the following formula:

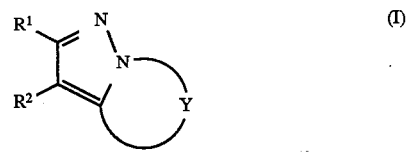

(I)

and a pharmaceutical composition containing the same and to uses thereof.

6 Claims, No Drawings

PYRAZOLE DERIVATIVES

This is a division, of application Ser. No. 08/269,520 filed on Jul. 1, 1994, now U.S. Pat. No. 5,478,827, which is a division of application Ser. No. 07/931,093, filed Aug. 17, 1992, now U.S. Pat. No. 5,356,897.

This invention relates to new heterocyclic derivatives. More particularly, this invention relates to pyrazole derivatives and pharmaceutically acceptable salts thereof which have pharmacological activities, processes for preparation thereof, a pharmaceutical composition comprising the same and a use of the same.

Accordingly, one object of this invention is to provide the new and useful pyrazole derivatives and pharmaceutically acceptable salts thereof which possess a strong inhibitory activity on the production of Interleukin-1 (IL-1) and a strong inhibitory activity on the production of tumor necrosis factor (TNF).

Another object of this invention is to provide processes for preparation of the pyrazole derivatives and salts thereof.

A further object of this invention is to provide a pharmaceutical composition comprising said pyrazole derivatives or a pharmaceutically acceptable salt thereof.

Still further object of this invention is to provide a use of said pyrazole derivatives or a pharmaceutically acceptable salt thereof as a medicament for prophylactic and therapeutic treatment of IL-1 and TNF mediated diseases such as chronic inflammatory diseases, specific autoimmune diseases, sepsis-induced organ injury, and the like in human being and animals.

The object pyrazole derivatives of the present invention are novel and can be represented by the following general formula (I):

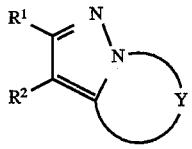
(I)

wherein
- $R^1$ is aryl which may have suitable substituent(s) or heterocyclic group which may have suitable substituent(s),
- $R^2$ is aryl which may have suitable substituent(s) or heterocyclic group which may have suitable substituent(s), and
- Y is a bivalent radical selected from

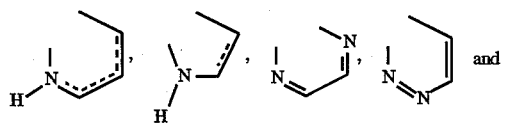 and

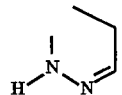

(in which ---- means single bond or double bond), each of which may have suitable substituent(s).

The object compound (I) of the present invention can be prepared by the following processes.

Process (1)

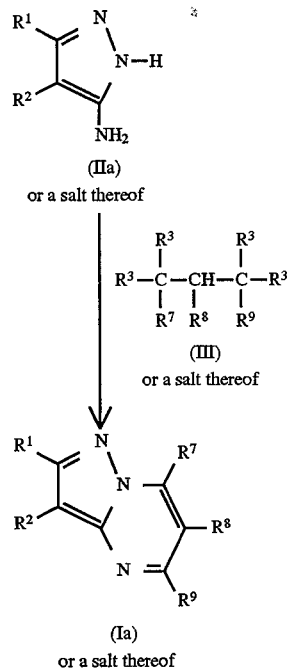

Process (2)

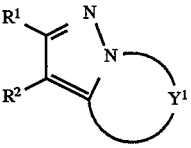

(Ib)
or a salt thereof

↓ reduction

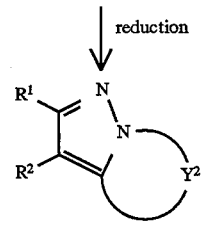

(Ic)
or a salt thereof

Process (3)
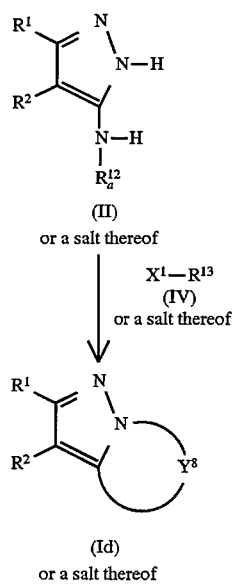
Process (4)
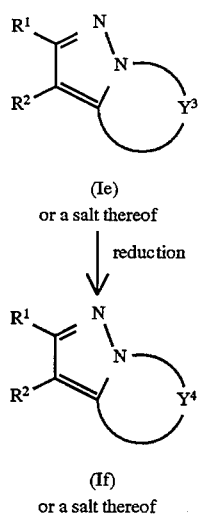
Process (5)
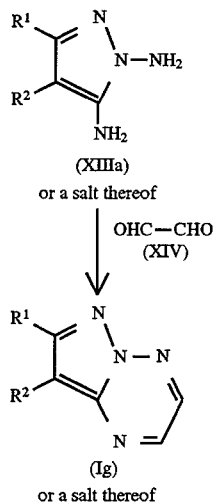
Process (6)
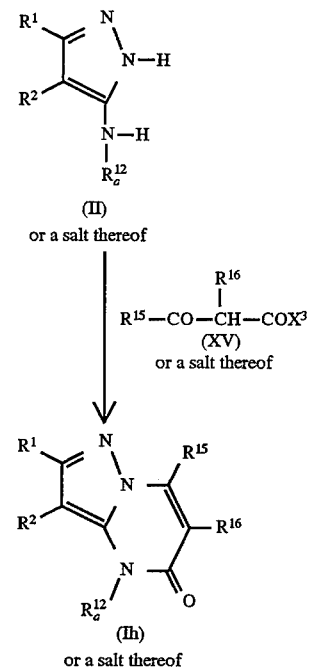

Process (7)
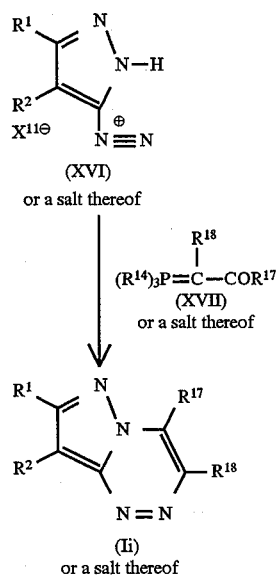
(XVI) or a salt thereof
↓ (R^14)_3P=C(R^18)—COR^17
(XVII) or a salt thereof
(Ii) or a salt thereof
Process (8)
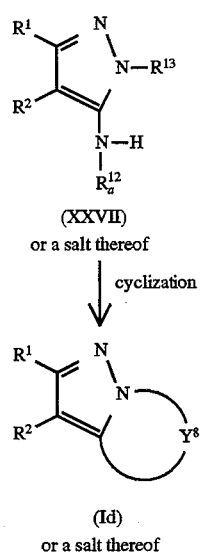
(XXVII) or a salt thereof
↓ cyclization
(Id) or a salt thereof
Process (9)
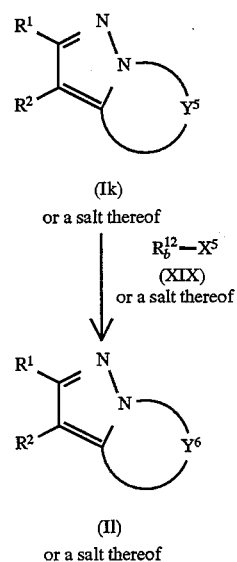
(Ik) or a salt thereof
↓ $R_b^{12}—X^5$ (XIX) or a salt thereof
(Il) or a salt thereof
Process (10)
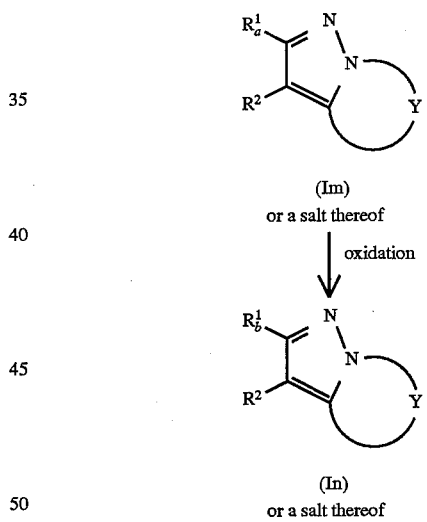
(Im) or a salt thereof
↓ oxidation
(In) or a salt thereof

Process (11)
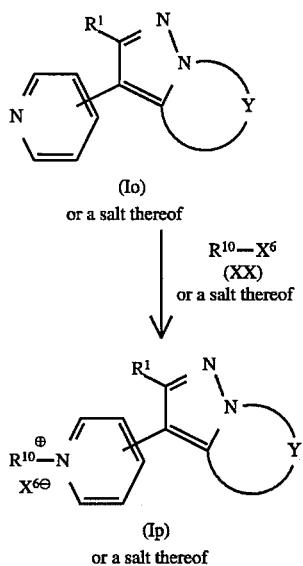
(Io)
or a salt thereof
↓ R¹⁰—X⁶
(XX)
or a salt thereof
(Ip)
or a salt thereof
Process (12)
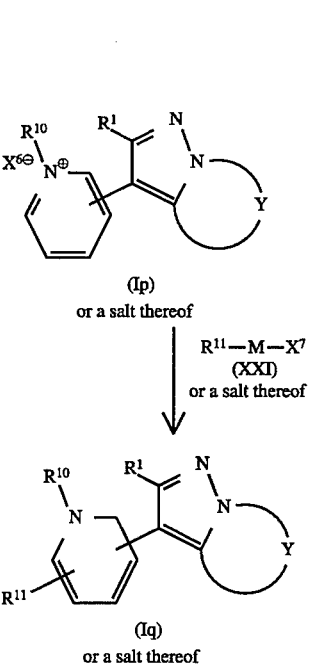
(Ip)
or a salt thereof
↓ R¹¹—M—X⁷
(XXI)
or a salt thereof
(Iq)
or a salt thereof
Process (13)
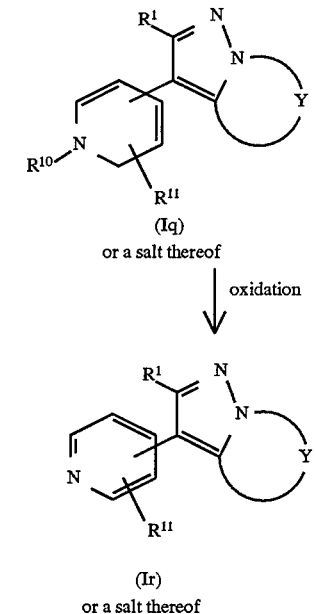
(Iq)
or a salt thereof
↓ oxidation
(Ir)
or a salt thereof
Process (14)
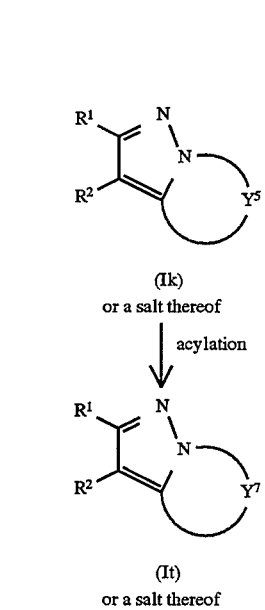
(Ik)
or a salt thereof
↓ acylation
(It)
or a salt thereof

Process (15)

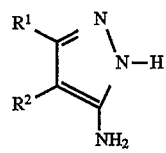

(IIa)
or a salt thereof

↓ Propandial which may have
suitable substituent(s)
(XXVIII)
or a salt thereof

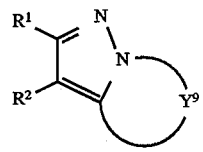

(Iu)
or a salt thereof

Process (16)

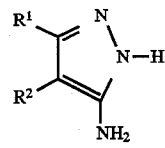

(IIa)
or a salt thereof

↓ Acrylaldehyde which
may have suitable
substituent(s)
(XXIX)
or a salt thereof

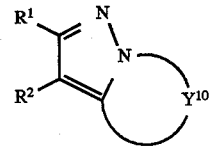

(Iv)
or a salt thereof

Process (17)

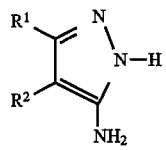

(IIa)
or a salt thereof

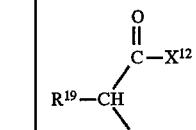

(XXX)
or a salt thereof

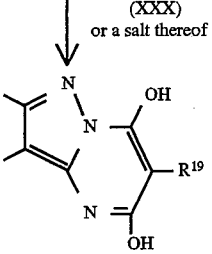

(Iw)
or a salt thereof

Process (18)

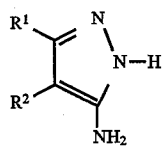

(IIa)
or a salt thereof

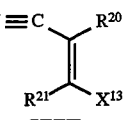

(XXXI)
or a salt thereof

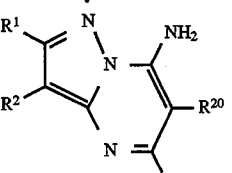

(Ix)
or a salt thereof

Process (19)
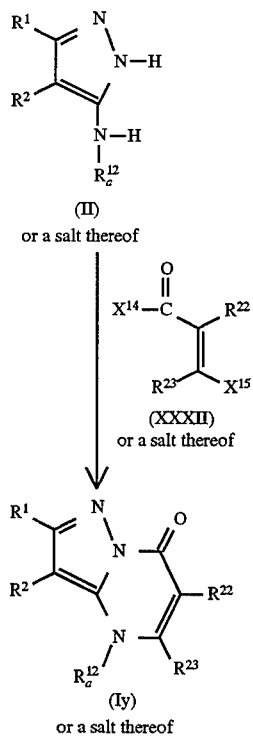
Process (20)
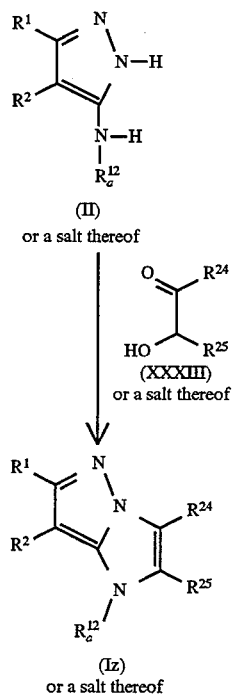
Process (21)
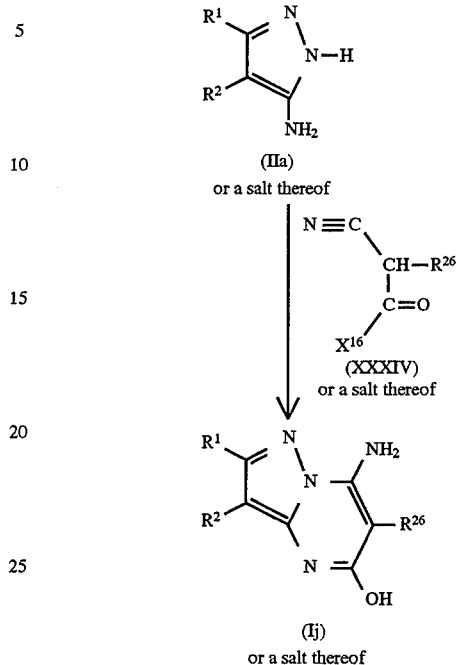
Process (22)
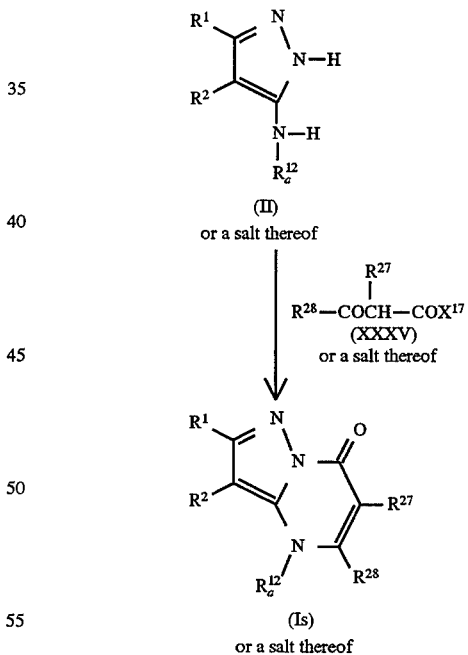
wherein
$R^1$, $R^2$ and Y are each as defined above,
$R^3$ is a leaving group,
$X^1$ and $X^7$ are each halogen,
$X^3$, $X^5$ and $X^6$ are each a leaving group,
$X^{11}$ is an acid residue,
$R^7$, $R^8$, $R^9$, $R_a^{12}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are each hydrogen or substituent, $R^{10}$ is acyl,
$R^{11}$ is lower alkyl,
$R_b^{12}$ is lower alkyl,
$R_a^1$ is lower alkylthioaryl,
$R_b^1$ is lower alkylsulfinylaryl or lower alkylsulfonylaryl,
M is alkali earth metal,
$X^{12}, X^{13}, X^{14}, X^{15}, X^{16}$ and $X^{17}$ are each a leaving group,
$R^{13}$ is esterified carboxyethenyl, esterified carboxyethyl or esterified carboxymethyl, each of which may have suitable substituent(s),
$R^{14}$ is lower alkyl or aryl,
$Y^1$ is a bivalent radical selected from

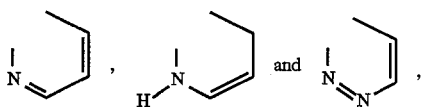

each of which may have suitable substituent(s),
$Y^2$ is a bivalent radical selected from

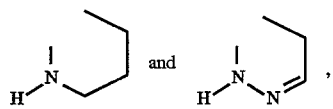

each of which may have suitable substituent(s),
$Y^3$ is a bivalent radical selected from

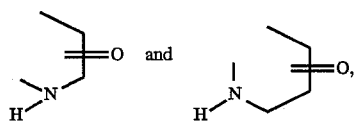

each of which may have suitable substituent(s),
$Y^4$ is a bivalent radical selected from

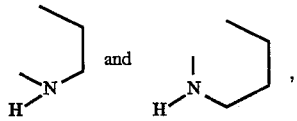

each of which may have suitable substituent(s),
$Y^5$ is a bivalent radical selected from

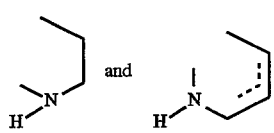

(in which ---- is as defined above), each of which may have an oxo group,
$Y^6$ is a bivalent radical selected from

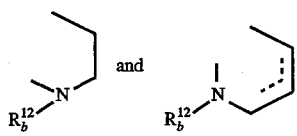

(in which $R_b^{12}$ and ---- are each as defined above), each of which may have an oxo group, $Y^7$ is a bivalent radical selected from

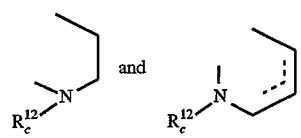

(in which ---- is as defined above and $R_c^{12}$ is acyl), each of which may have an oxo group.
$Y^8$ is a bivalent radical selected from

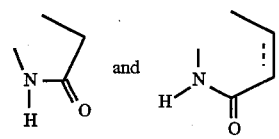

(in which ---- is as defined above), each of which may have suitable substituent(s),
$Y^9$ is

which may have suitable substituent(s) and
$Y^{10}$ is

which may have suitable substituent(s).

The starting compounds or salts thereof can be prepared by the following Processes.

Process (A)

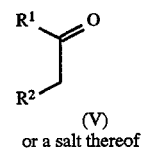

(V)
or a salt thereof

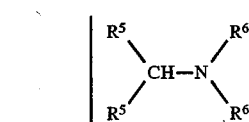

(VI)
or a salt thereof

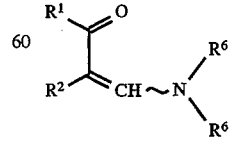

(VII)
or a salt thereof

Process (B)

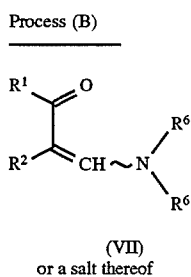

(VII)
or a salt thereof

↓ H₂NOH (VIII) or a salt thereof

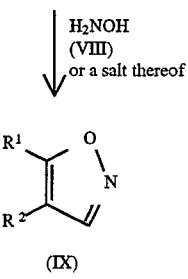

(IX)
or a salt thereof

Process (C)

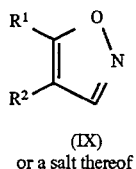

(IX)
or a salt thereof

↓ Cleavage reaction of O—N bond

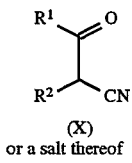

(X)
or a salt thereof

Process (D)

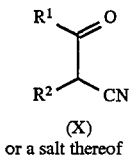

(X)
or a salt thereof

① ↓ halogenation

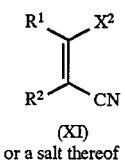

(XI)
or a salt thereof

② ↓ H₂NNH₂ (XII) or a salt thereof

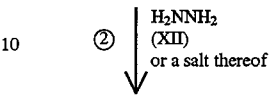

(IIa)
or a salt thereof

Process (E)

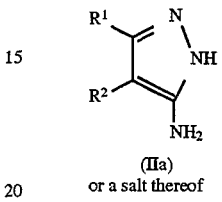

(XXII)
or a salt thereof

↓ R²—CH₂CN (XXIII) or a salt thereof

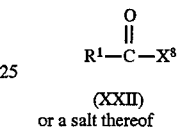

(X)
or a salt thereof

Process (F)

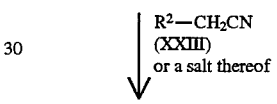

(X)
or a salt thereof

↓ NH₂NH₂ (XII) or a salt thereof

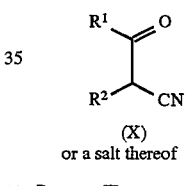

(IIa)
or a salt thereof

Process (G)

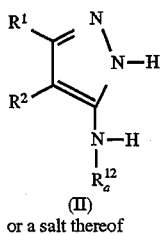

(II)
or a salt thereof

↓ H$_2$N—X$^9$
(XXIV)
or a salt thereof

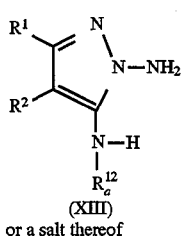

(XIII)
or a salt thereof

Process (H)

R$^{16}$—CH$_2$—COX$^3$
(XXV)
or a salt thereof

↓ R$^{15}$—CO—X$^{10}$
(XXVI)
or a salt thereof

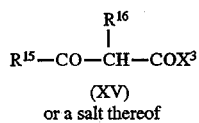

(XV)
or a salt thereof

Process (I)

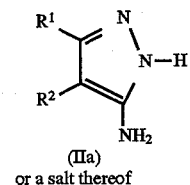

(IIa)
or a salt thereof

↓ diazotization

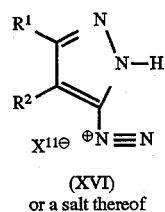

(XVI)
or a salt thereof

Process (J)

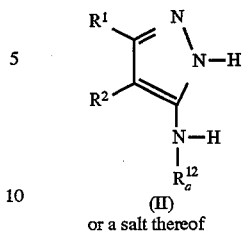

(II)
or a salt thereof

↓ CH$_2$=CHCOX$^4$
(XVIII)
or a salt thereof

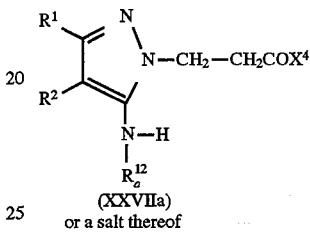

(XXVIIa)
or a salt thereof wherein

R$^1$, R$^2$, R$_a^{12}$, X$^3$, X$^{11}$, R$^{15}$ and R$^{16}$ are each as defined above, X$^4$, R$^5$, X$^8$, X$^9$ and X$^{10}$ are each a leaving group, R$^6$ is lower alkyl, and X$^2$ is halogen.

Suitable pharmaceutically acceptable salts of the object compound (I) are conventional non-toxic salts and may include e.g. a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, toluenesulfonate, etc.); a salt with a basic or acidic amino acid (e.g. arginine, aspartic acid, glutamic acid, etc.).

In the above and subsequent descriptions of the present specification, suitable example and illustration of the various definitions which the present invention intends to include within the scope thereof are explained in detail as follows.

The term "lower" is used to intend a group having 1 to 6, preferably 1 to 4, carbon atom(s), unless otherwise provided.

Suitable "lower alkyl" and "lower alkyl moiety" in the terms "lower alkylthioaryl", "lower alkylsulfinylaryl" and "lower alkylsulfonylaryl" may include straight or branched one such as methyl, ethyl, propyl, isopropyl, butyl, t-butyl, pentyl, hexyl, and the like, in which more preferable example may be C$_1$–C$_4$ alkyl.

Suitable "heterocyclic group" means saturated or unsaturated, monocyclic or polycyclic heterocyclic group containing at least one hetero-atom such as an oxygen, sulfur, nitrogen atom and the like. And, especially preferable heterocyclic group may be heterocyclic group such as unsaturated 3 to 8-membered more preferably 5 or 6-membered heteromonocyclic group containing 1 to 4-nitrogen atom(s), for example, pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered (more preferably 5 or 6-membered)heteromonocyclic group containing 1 to 4 nitrogen atom(s), for example pyrrolidinyl, imidazolidinyl, piperidino, piperazinyl, etc.; unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered)heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.;

saturated 3 to 8-membered (more preferably 5 or 6-membered)heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered)heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 to 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example benzothienyl, benzodithiinyl, etc.;

unsaturated condensed heterocyclic group containing an oxygen atom and 1 to 2 sulfur atom(s), for example, benzoxathiinyl, etc. and the like.

Suitable "acyl" may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Carbamoyl;

Aliphatic acyl such as lower or higher alkanoyl (e.g. formyl, acetyl, propanoyl, butanoyl, 2-methylpropanoyl, pentanoyl, 2,2-dimethylpropanoyl, hexanoyl heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

lower or higher alkoxycarbonyl (e.g. methoxycarbonyl, ethoxycarbonyl, t-butoxycarbonyl, t-pentyloxycarbonyl, heptyloxycarbonyl, etc.);

lower or higher alkanesulfonyl (e.g. methanesulfonyl, ethanesulfonyl, etc.);

lower or higher alkoxysulfonyl (e.g. methoxysulfonyl, ethoxysulfonyl, etc.); or the like;

Aromatic acyl such as aroyl (e.g. benzoyl, toluoyl, naphthoyl, etc.);

ar(lower)alkanoyl [e.g. phenyl(lower)alkanoyl (e.g. phenylacetyl, phenylpropanoyl, phenylbutanoyl, phenylisobutylyl, phenylpentanoyl, phenylhexanoyl, etc.), naphtyl(lower)alkanoyl (e.g. naphthylacetyl, naphthylpropanoyl, naphthylbutanoyl, etc.), etc.];

ar(lower)alkenoyl [e.g. phenyl(lower)alkenoyl (e.g. phenylpropenoyl, phenylbutenoyl, phenylmethacryloyl, phenylpentenoyl, phenylhexenoyl, etc.), naphthyl(lower)alkenoyl (e.g. naphthylpropenoyl, naphthylbutenoyl, naphthylpentenoyl, etc.), etc.];

ar(lower)alkoxycarbonyl [e.g. phenyl(lower) alkoxycarbonyl (e.g. benzyloxycarbonyl, etc.), etc.]; aryloxycarbonyl (e.g. phenoxycarbonyl, naphthyloxycarbonyl, etc.);

aryloxy(lower)alkanoyl (e.g. phenoxyacetyl, phenoxypropionyl, etc.);

arylcarbamoyl (e.g. phenylcarbamoyl, etc.);

arylthiocarbamoyl (e.g. phenylthiocarbamoyl, etc.);

arylglyoxyloyl (e.g. phenylglyoxyloyl, naphthylglyoxyloyl, etc.);

arenesulfonyl (e.g. benzenesulfonyl, p-toluenesulfonyl, etc.); or the like;

Heterocyclic acyl such as heterocycliccarbonyl;

heterocyclic(lower)alkanoyl (e.g. thienylacetyl, thienylpropanoyl, thienylbutanoyl, thienylpentanoyl, thienylhexanoyl, thiazolylacetyl, thiadiazolylacetyl, tetrazolylacetyl, etc.);

heterocyclic(lower)alkenoyl (e.g. heterocyclicpropenoyl, heterocyclicbutenoyl, heterocyclicpentenoyl, heterocyclichexenoyl, etc.);

heterocyclicglyoxyloyl (e.g. thiazolylglyoxyloyl, thienylglyoxyloyl, etc.); or the like; in which suitable heterocyclic moiety in the terms "heterocycliccarbonyl", "heterocyclic(lower) alkanoyl", heterocyclic(lower)alkenoyl and "heterocyclicglyoxyloyl" as mentioned above means, in more detail, saturated or unsaturated, monocyclic or polycyclic heterocyclic group containing at least one heteroatom such as an oxygen, sulfur, nitrogen atom and the like.

Suitable "aryl" and "aryl moiety" in the terms "lower alkylthioaryl", "lower alkylsulfinylaryl" and "lower alkylsulfonylaryl" may include phenyl, naphthyl and the like, in which more preferable example may be phenyl.

Suitable "substituent" in the term "aryl which may have suitable substituent(s)" may include lower alkyl (e.g., methyl, ethyl, propyl, isopropyl, butyl, isobutyl, tert-butyl, pentyl, neopentyl, tert-pentyl, hexyl, etc.), lower alkoxy (e.g., methoxy, ethoxy, propoxy, isopropoxy, isobutoxy, tert-butoxy, pentyloxy, neopentyloxy, tert-pentyloxy, hexyloxy, etc.), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl, etc.), mono(or di or tri)halo(lower)alkyl (e.g., fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, etc.), halogen (e.g., chlorine, bromine, fluorine and iodine), carboxy, protected carboxy, hydroxy, protected hydroxy, aryl (e.g., phenyl, naphthyl, etc.), ar(lower)alkyl such as phenyl(lower)alkyl (e.g, benzyl, phenethyl, phenylpropyl, etc.), carboxy(lower)alkyl, protected carboxy(lower)alkyl, amino, protected amino, di(lower)alkylamino (e.g., dimethylamino, diethylamino, diisopropylamino, ethylmethylamino, isopropylmethylamino, ethylisopropylamino, etc.), hydroxy(lower)alkyl, protected hydroxy(lower)alkyl, nitro, acyl as exemplified above, cyano, mercapto, lower alkylthio (e.g., methylthio, ethylthio, propylthio, isopropylthio, butylthio, etc.), lower alkylsulfinyl (e.g., methylsulfinyl, ethylsulfinyl, propylsulfinyl, isopropylsulfinyl, butylsulfinyl, etc.), lower alkylsulfonyl (e.g., methylsulfonyl, ethylsulfonyl, propylsulfonyl, isopropylsulfonyl, butylsulfonyl, etc.), imino, and the like.

Suitable "substituent" in the term "heterocyclic group which may have suitable substituent(s)" may include lower alkyl (e.g., methyl, ethyl, propyl, isopropy, butyl, isobutyl, tert-butyl, pentyl, neopentyl, tert-pentyl, hexyl, etc.), lower alkoxy (e.g., methoxy, ethoxy, propoxy, isopropoxy, isobutoxy, tert-butoxy, pentyloxy, neopentyloxy, tert-pentyloxy, hexyloxy, etc.), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl, etc.), mono(or di or tri)halo(lower)alkyl (e.g., fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, etc.), halogen (e.g., chlorine, bromine, fluorine and iodine), carboxy, protected carboxy, hydroxy, protected hydroxy, aryl (e.g, phenyl, naphthyl, etc.), ar(lower)alkyl such as phenyl(lower)alkyl (e.g., benzyl, phenethyl, phenylpropyl, etc.), carboxy(lower)alkyl, protected carboxy(lower)alkyl, amino, protected amino, di(lower)alkylamino (e.g., dimethylamino, diethylamino, diisopropylamino, ethylmethylamino, isopropylmethylamino, ethylisopropylamino, etc.), hydroxy(lower)alkyl, protected hydroxy(lower)alkyl, nitro, acyl as exemplified above, cyano, mercapto, lower alkylthio, (e.g., methylthio, ethylthio, propylthio, isopropylthio, butylthio, etc.), lower alkylsulfinyl (e.g., methylsulfinyl, ethylsulfinyl, propylsulfinyl, isopropylsulfinyl, butylsulfinyl, etc.), lower alkylsulfonyl (e.g., methylsulfonyl, ethylsulfonyl, propylsulfonyl, isopropylsulfonyl, butylsulfonyl, etc.), imino, and the like.

Suitable "protected carboxy" and "protected carboxy" moiety in the term "protected carboxy(lower)alkyl" may include esterified carboxy and the like. An suitable examples of said ester moiety may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.);

lower alkenyl ester (e.g., vinyl ester, allyl ester, etc.);

lower alkynyl ester (e.g., ethynyl ester, propynyl ester, etc.);

lower alkoxyalkyl ester (e.g., methoxymethyl ester, ethoxymethyl ester, isopropoxymethyl ester, 1-methoxyethyl ester, 1-ethoxyethyl ester, etc.);

lower alkylthioalkyl ester (e.g., methylthiomethyl ester, ethylthiomethyl ester, ethylthioethyl ester, isopropylthiomethyl ester, etc.);

mono(or di or tri)halo(lower)alkyl ester (e.g. 2-iodoethyl ester, 2,2,2-trichloroethyl ester, etc.);

lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);

lower alkanesulfonyl(lower)alkyl ester (e.g. mesylmethyl ester, 2-mesylethyl ester etc.);

ar(lower)alkyl ester, for example, phenyl(lower)alkyl ester which may have one or more suitable substituent (s) (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.);

aryl ester which may have one or more suitable substituent(s) such as substituted or unsubstituted phenyl ester (e.g., phenyl ester, tolyl ester, t-butylphenyl ester, xylyl ester, mesityl ester, cumenyl ester, 4-chlorophenyl ester, 4-methoxyphenyl ester, etc.);

tri(lower)alkyl silyl ester; lower alkylthioester (e.g. methylthioester, ethylthioester, etc.) and the like.

Suitable examples of ester moiety in the terms "esterified carboxyethenyl", "esterified carboxyethyl" and "esterified carboxymethyl" may be the same as exemplified above.

Suitable "protected amino" may include acylamino wherein acyl moiety can be referred to the ones as exemplified above, or the like.

Suitable "protected hydroxy" and "protected hydroxy" moiety in the term "protected hydroxy(lower)alkyl" may include acyloxy wherein acyl moiety can be referred to the ones as exemplified above, or the like.

Suitable "leaving group" may include lower alkoxy (e.g. methoxy, ethoxy, propoxy, isopropoxy, butoxy, isobutoxy, t-butoxy, pentoxy, etc.), aryloxy (e.g. phenoxy, naphthoxy, etc.), an acid residue or the like. Suitable "acid residue" may be halogen (e.g. chlorine, bromine, iodine, etc.), sulfonyloxy (e.g. methanesulfonyloxy, benzenesulfonyloxy, mesitylenesulfonyloxy, toluenesulfonyloxy, etc.) or the like.

Suitable "halogen" may be the same as exemplified above.

Suitable "alkali earth metal" may include magnesium, calcium, and the like.

Suitable "substituent in the definition of $R^7$, $R^8$, $R^9$, $R_a^{12}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ may include lower alkyl (e.g., methyl, ethyl, propyl, isopropyl, butyl, isobutyl, tert-butyl, pentyl, neopentyl, tert-pentyl, hexyl, etc. ), lower alkoxy (e.g., methoxy, ethoxy, propoxy, isopropoxy, isobutoxy, tert-butoxy, pentyloxy, neopentyloxy, tert-pentyloxy, hexyloxy, etc.), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl, etc. ), mono(or di or tri) halo(lower)alkyl (e.g. fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, 2,2,3,3,3-pentafluoropropyl, etc.), halogen (e.g., chlorine, bromine, fluorine and iodine), carboxy, protected carboxy, hydroxy, protected hydroxy, aryl (e.g., phenyl, naphthyl, etc.) which may have halogen, ar(lower)alkyl such as phenyl(lower) alkyl (e.g., benzyl, phenethyl, phenylpropyl, etc.), carboxy (lower)alkyl wherein lower alkyl moiety can be referred to the ones as exemplified above, protected carboxy(lower) alkyl wherein lower alkyl moiety can be referred to the ones as exemplified above and protected carboxy moiety can be referred to the ones as exemplified above, amino, protected amino, di(lower)alkylamino (e.g. dimethylamino, diethylamino, diisopropylamino, ethylmethylamino, isopropylmethylamino, ethylisopropylamino, etc.), hydroxy (lower)alkyl, protected hydroxy(lower)alkyl, nitro, acyl as exemplified above, cyano, mercapto, lower alkylthio (e.g., methylthio, ethylthio, propylthio, isopropylthio, butylthio, etc.), imino, and the like.

Suitable "substituent" in the terms "propandial which may have suitable substituent(s)", "acrylaldehyde which may have suitable substituent(s)" and "esterified carboxyethenyl, esterified carboxyethyl or esterified carboxymethyl, each of which may have suitable substituent(s)" may include lower alkyl (e.g., methyl, ethyl, propyl, isopropyl, butyl, isobutyl, tert-butyl, pentyl, neopentyl, tert-pentyl, hexyl, etc.), lower alkoxy (e.g., methoxy, ethoxy, propoxy, isopropoxy, isobutoxy, tert-butoxy, pentyloxy, neopentyloxy, tert-pentyloxy, hexyloxy, etc.), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl, etc. ), mono(or di or tri)halo(lower)alkyl (e.g. fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, 2,2,3,3,3-pentafluoropropyl, etc.), halogen (e.g., chlorine, bromine, fluorine and iodine), carboxy, protected carboxy, hydroxy, protected hydroxy, aryl (e.g., phenyl, naphthyl, etc.) which may have halogen, ar(lower)alkyl such as phenyl(lower) alkyl (e.g., benzyl, phenethyl, phenylpropyl, etc.), carboxy (lower)alkyl wherein lower alkyl moiety can be referred to the ones as exemplified above, protected carboxy(lower) alkyl wherein lower alkyl moiety can be referred to the ones as exemplified above and protected carboxy moiety can be referred to the ones as exemplified above, amino, protected amino, di(lower)alkylamino (e.g., dimethylamino, diethylamino, diisopropylamino, ethylmethylamino, isopropylmethylamino, ethylisopropylamino, etc.), hydroxy (lower)alkyl, protected hydroxy(lower)alkyl, nitro, acyl as exemplified above, cyano, mercapto, lower alkylthio (e.g., methylthio, ethylthio, propylthio, isopropylthio, butylthio, etc.), imino, and the like.

Suitable "substituent" in the terms "bivalent radical selected from

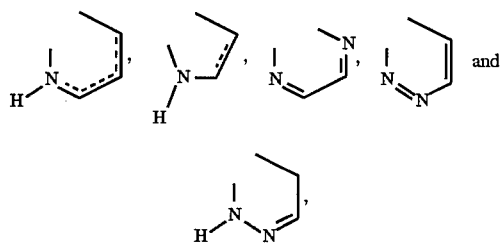

each of which may have suitable substituent(s)", "bivalent radical selected from

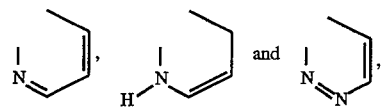

each of which may have suitable substituent(s)", "bivalent radical selected from

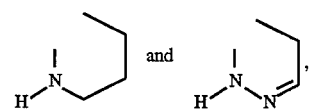

each of which may have suitable substituent(s)", "bivalent radical selected from

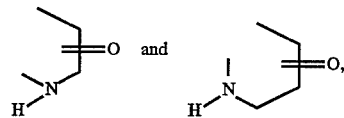

each of which may have suitable substituent(s)", "bivalent radical selected from

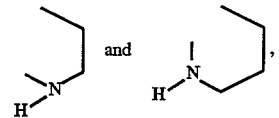

each of which may have suitable substituent(s)", "bivalent radical selected from

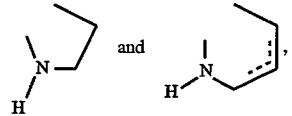

each of which may have suitable substituent(s)", "bivalent radical selected from

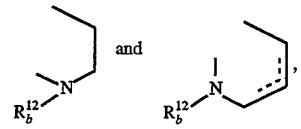

each of which may have suitable substituent(s)", "bivalent radical selected from

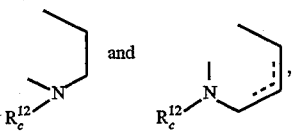

each of which may have suitable substituent(s)", "bivalent radical selected from

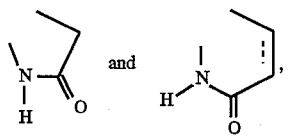

each of which may have suitable substituent(s),

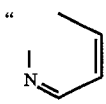

which may have suitable substituent(s)" and

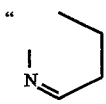

which may have suitable substituent(s)" may include lower alkyl (e.g., methyl, ethyl, propyl, isopropyl, butyl, isobutyl, tert-butyl, pentyl, neopentyl, tert-pentyl, hexyl, etc.), lower alkoxy (e.g., methoxy, ethoxy, propoxy, isopropoxy, isobutoxy, tert-butoxy, pentyloxy, neopentyloxy, tert-pentyloxy, hexyloxy, etc.), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl, etc.), mono(or di or tri)halo(lower)alkyl (e.g. fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, 2,2,3,3, 3-pentafluoropropyl, etc.), halogen (e.g., chlorine, bromine, fluorine and iodine), carboxy, protected carboxy, hydroxy, protected hydroxy, aryl (e.g., phenyl, naphthyl, etc.) which may have halogen, ar(lower)alkyl such as phenyl(lower) alkyl (e.g., benzyl, phenethyl, phenylpropyl, etc.), carboxy (lower)alkyl wherein lower alkyl moiety can be referred to the ones as exemplified above, protected carboxy(lower) alkyl wherein lower alkyl moiety can be referred to the ones as exemplified above and protected carboxy moiety can be referred to the ones as exemplified above, amino, protected amino, di(lower)alkylamino (e.g., dimethylamino, diethylamino, diisopropylamino, ethylmethylamino, isopropylmethylamino, ethylisopropylamino, etc.), hydroxy (lower)alkyl, protected hydroxy(lower)alkyl, nitro, acyl as exemplified above, oxo, cyano, mercapto, lower alkylthio (e.g., methylthio, ethylthio, propylthio, isopropylthio, butylthio, etc.), imino, and the like.

The processes for preparing the object and starting compounds are explained in detail in the following.

Process (1)

The compound (Ia) or a salt thereof can be prepared by reacting the compound (IIa) or a salt thereof with the compound (III) or a salt thereof.

This reaction is usually carried out in a solvent such as alcohol (e.g., methanol, ethanol, etc.), benzene, N,N-dimethylformamide, tetrahydrofuran, methylene chloride, ethylene chloride, chloroform, diethyl ether or any other solvent which does not adversely affect the reaction.

The reaction temperature is not critical and the reaction is usually carried out under cooling to heating.

The reaction is usually carried out in the presence of an acid including Lewis acid.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, zinc halide (e.g. zinc chloride, zinc bromide, etc.), etc.] and the like.

Process (2)

The compound (Ic) or a salt thereof can be prepared by subjecting the compound (Ib) or a salt thereof to reduction reaction.

Reduction is carried out in a conventional manner, including chemical reduction and catalytic reduction.

Suitable reducing agents to be used in chemical reduction are hydrides (e.g. hydrogen iodide, hydrogen sulfide, lithium aluminum hydride, sodium borohydride, lithium borohydride, diborane, sodium cyanoborohydride, etc.) or a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluene-sulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc) and the like.

The reaction is usually carried out in a solvent such as water, alcohol (e.g. methanol, ethanol, etc.), N,N-dimethylformamide, tetrahydrofuran, a mixture thereof or any other solvent which does not adversely affect the reaction.

Additionally, in case that the above-mentioned acids to be used in chemical reduction are in liquid, they can also be used as a solvent.

The reaction temperature of this reaction is not critical and the reaction is usually carried out under cooling to heating.

Process (3)

The compound (Id) or a salt thereof can be prepared by reacting the compound (II) or a salt thereof with the compound (IV) or a salt thereof.

The reaction is usually carried out in a conventional solvent such as alcohols (e.g. methanol, ethanol, ethylene glycol, etc.), chloroform, ether, tetrahydrofuran, benzene or any other organic solvent which does not adversely influence the reaction.

The reaction temperature is not critical and the reaction is usually carried out under cooling to heating.

The reaction may be also carried out in the presence of an inorganic or an organic base such as an alkali metal hydroxide, an alkali metal hydrogencarbonate, alkali metal carbonate, tri(lower)alkylamine, alkali metal hydride (e.g.

sodium hydride, etc.), alkali metal (lower)alkoxide (e.g. sodium methoxide, sodium ethoxide, etc.), pyridine lutidine, picoline, dimethylaminopyridine, N-(lower)alkylmorpholine, N,N-di(lower)alkylbenzylamine, N,N-di(lower)alkylaniline or the like. When the base and/or the starting compound are in liquid, they can be used also as a solvent.

Process (4)

The compound (If) or a salt thereof can be prepared by subjecting the compound (Ie) or a salt thereof to reduction reaction.

This reduction can be carried out in a similar manner to that of the aforementioned Process (2), and therefore the reagents to be used and the reaction conditions (e.g., solvent, reaction temperature, etc.) can be referred to those of the Process (2).

Process (5)

The compound (Ig) or a salt thereof can be prepared by reacting the compound (XIIIa) or a salt thereof with the compound (XIV).

This reaction is usually carried out in a solvent such as water, alcohol (e.g., methanol, ethanol, etc.), benzene, N,N-dimethylformamide, tetrahydrofuran, toluene, methylenechloride, ethylene dichloride, chloroform, diethyl ether or any other solvent which does not adversely affect the reaction.

The reaction temperature is not critical and the reaction is usually carried out under warming to heating.

Process (6)

The compound (Ih) or a salt thereof can be prepared by reacting the compound (II) or a salt thereof with the compound (XV) or a salt thereof.

This reaction is usually carried out in a solvent such as water, alcohol (e.g., methanol, ethanol, etc.), benzene, N,N-dimethylformamide, tetrahydrofuran, toluene, methylenechloride, ethylene dichloride, chloroform, diethyl ether or any other solvent which does not adversely affect the reaction.

The reaction temperature is not critical and the reaction is usually carried out under warming to heating.

The reaction is usually carried out in the presence of an inorganic or an organic base such as an alkali metal (e.g., sodium, potassium, etc.), an alkali metal hydroxide (e.g., sodium hydroxide, potassium hydroxide, etc.), an alkali metal hydrogencarbonate (e.g., sodium hydrogencarbonate, potassium hydrogencarbonate, etc.), alkali metal carbonate (e.g., sodium carbonate, potassium carbonate, etc.), tri(lower)alkylamine (e.g., trimethylamine, triethylamine, diisopropylethylamine, etc.), alkali metal hydride (e.g., sodium hydride, etc.), alkali metal (lower)alkoxide (e.g., sodium methoxide, sodium ethoxide, etc.), pyridine, lutidine, picoline, dimethylaminopyridine, N-(lower)alkylmorpholine, N,N-di(lower)alkylbenzylamine, N,N-di(lower)alkylaniline or the like.

When the base and/or the starting compound are in liquid, they can be also as a solvent.

Process (7)

The compound (Ii) or a salt thereof can be prepared by reacting the compound (XVI) or a salt thereof with the compound (XVII) or a salt thereof.

This reaction is usually carried out in a solvent such as water, alcohol (e.g., methanol, ethanol, etc.), benzene, N,N-dimethylformamide, tetrahydrofuran, toluene, methylenechloride, ethylene dichloride, chloroform, diethyl ether or any other solvent which does not adversely affect the reaction.

The reaction temperature is not critical and the reaction is usually carried out under cooling to warming.

Process (8)

The compound (Id) or a salt thereof can be prepared by subjecting the compound (XXVII) or a salt thereof to cyclization reaction.

This reaction is usually carried out by a method using the catalyst such as an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.] and the like.

When the acid and/or the starting compound are in liquid, they can be also as a solvent.

This reaction is usually carried out in a solvent such as water, alcohol (e.g, methanol, ethanol, etc.), benzene, N,N-dimethylformamide, tetrahydrofuran, toluene, methylenechloride, ethylene dichloride, chloroform, diethyl ether or any other solvent which does not adversely affect the reaction.

The reaction temperature is not critical and the reaction is usually carried out under warming to heating.

Process (9)

The compound (Ij) or a salt thereof can be prepared by reacting the compound (Ik) or a salt thereof with the compound (XIX) or a salt thereof.

This reaction is usually carried out in a solvent such as benzene, N,N-dimethylformamide, tetrahydrofuran, toluene, methylenechloride, ethylene dichloride, chloroform, diethyl ether or any other solvent which does not adversely affect the reaction.

The reaction temperature is not critical and the reaction is usually carried out under cooling to warming.

The reaction is usually carried out in the presence of an inorganic or an organic base such as an alkali metal, an alkali metal hydroxide, an alkali metal hydrogencarbonate, alkali metal carbonate, tri(lower)alkylamine, alkali metal hydride (e.g. sodium hydride, etc.), alkali metal (lower)alkoxide (e.g. sodium methoxide, sodium ethoxide, etc.), pyridine, lutidine, picoline, dimethylaminopyridine, N-(lower)alkylmorpholine, N,N-di(lower)alkylbenzylamine, N,N-di(lower)alkylaniline or the like.

When the base and/or the starting compound are in liquid, they can be also used as a solvent.

Process (10)

The compound (In) or a salt thereof can be prepared by subjecting the compound (Im) or a salt thereof to oxidation reaction.

Oxidation is carried out in a conventional manner, which is capable of oxidizing a sulfur atom to an oxidized sulfur atom, and suitable oxidizing reagent may be oxygen acid such as periodate (e.g. sodium periodate, potassium periodate, etc.), peroxy acid such as peroxybenzoic acid (e.g., peroxybenzoic acid, m-chloroperoxybenzoic acid, etc.), and the like.

The reaction is usually carried out in a conventional solvent such as tetrahydrofuran, dioxane, dichloromethane, ethylene dichloride, chloroform, N,N-dimethylformamide, N,N-dimethylacetamide, or any other organic solvent which does not adversely affect the reaction.

The reaction temperature is not critical and the reaction is usually carried out under cooling to warming.

Process (11)

The compound (Ip) or a salt thereof can be prepared by reacting the compound (Io) or a salt thereof with the compound (XX) or a salt thereof.

This reaction is usually carried out in a solvent such as benzene, N,N-dimethylformamide, tetrahydrofuran, toluene, methylenechloride, ethylene dichloride, chloroform, diethyl ether or any other solvent which does not adversely affect the reaction.

The reaction temperature is not critical and the reaction is usually carried out under cooling to warming.

Process (12)

The compound (Iq) or a salt thereof can be prepared by reacting the compound (Ip) or a salt thereof with the compound (XXI) or a salt thereof.

This reaction is usually carried out in a solvent such as benzene, N,N-dimethylformamide, tetrahydrofuran, toluene, methylenechloride, ethylene dichloride, chloroform, diethyl ether or any other solvent which does not adversely affect the reaction.

The reaction temperature is not critical and the reaction is usually carried out under cooling to warming.

Process (13)

The compound (Ir) or a salt thereof can be prepared by subjecting the compound (Iq) or a salt thereof to oxidation reaction.

Oxidation is carried out in a conventional manner, which is capable of oxidizing N-acyl substituted dihydropyridine to pyridine, and suitable oxidizing reagent may be sulfur, oxygen, alkali metal alkoxide, (e.g., potassium t-butoxide, etc.), or the like.

The reaction is usually carried out in a conventional solvent such as water, alcohol (e.g., methanol, ethanol, isopropyl alcohol, t-butyl alcohol, etc.), tetrahydrofuran, dioxane, dichloromethane, chloroform, N,N-dimethylacetamide, N,N-dimethylformamide, decalin, tetralin or any other organic solvent which does not adversely affect the reaction.

Among these solvents, hydrophilic solvents may be used in a mixture with water.

The reaction temperature is not critical and the reaction is usually carried out under warming to heating.

Process (14)

The compound (It) or a salt thereof can be prepared by subjecting the compound (Ik) or its reactive derivative at the imino group or a salt thereof to acylation reaction.

Suitable acylating agent to be used in the present acylation reaction may include the compound of the formula:

 $R_c^{12}$—OH     (XXXVI)

(wherein $R_c^{12}$ is acyl) or its reactive derivative or a salt thereof.

Suitable reactive derivative at the imino group of the compound (Ik) may include a silyl derivative formed by the reaction of the compound (Ik) with a silyl compound such as N,O-bis(trimethylsilyl)acetamide, N-trimethylsilylacetamide or the like; a derivative formed by the reaction of the compound (Ik) with phosphorus trichloride or phosgene, and the like.

suitable reactive derivative of the compound (XXXVI) may include an acid halide, an acid anhydride, an activated amide, an activated ester, isocyanate, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g. methanesulfonic acid, ethanesulfonic acid, etc.), sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole, or an activated ester (e.g. cyanomethyl ester, methoxymethyl ester, dimethyliminomethyl [(CH$_3$)$_2$N$^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); substituted or unsubstituted aryl isocyanate; substituted or unsubstituted aryl isothiocyanate, and the like. These reactive derivatives can optionally be selected from them according to the kind of the compound (XXXVI) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide pyridine or any other organic solvents which do not adversely influence the reaction. These conventional solvents may also be used in a mixture with water.

When the compound (XXXVI) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine, diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxasolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine (e.g., trimethylamine, triethylamine, etc.), pyridine, N-(lower)alkylmorphorine, N,N-di(lower)alkylbenzylamine, or the like. The reaction temperature is not critical, and the reaction is usually carried out under cooling to heating.

Process (15)

The compound (Iu) or a salt thereof can be prepared by reacting the compound (IIa) or a salt thereof with the compound (XXVIII) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvent which does not adversely affect the reaction. These conventional solvent may also be used in a mixture with water.

The reaction temperature is not critical and the reaction is usually carried out under warming to heating.

The reaction is usually carried out in the presence of an acid including Lewis acid.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, zinc halide (e.g. zinc chloride, zinc bromide, etc.), etc.] and the like.

When the acid and/or the starting compound are in liquid, they can be also used as a solvent.

Process (16)

The compound (Iv) or a salt thereof can be prepared by reacting the compound (IIa) or a salt thereof with the compound (XXIX) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, diethyl ether or any other solvent which does not adversely affect the reaction.

The reaction temperature is not critical and the reaction is usually carried out under warming to heating.

When the starting compound is in liquid, it can be also used as a solvent.

Process (17)

The compound (Iw) or a salt thereof can be prepared by reacting the compound (IIa) or a salt thereof with the compound (XXX) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, diethyl ether or any other solvent which does not adversely affect the reaction.

The reaction temperature is not critical and the reaction is usually carried out under warming to heating.

Process (18)

The compound (Ix) or a salt thereof can be prepared by reacting the compound (IIa) or a salt thereof with the compound (XXXI) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvent which does not adversely affect the reaction. These conventional solvent may also be used in a mixture with water.

The reaction temperature is not critical and the reaction is usually carried out under warming to heating.

The reaction is usually carried out in the presence of an acid including Lewis acid.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, zinc halide (e.g. zinc chloride, zinc bromide, etc.), etc.] and the like.

When the acid and/or the starting compound are in liquid, they can be also used as a solvent.

Process (19)

The compound (Iy) or a salt thereof can be prepared by reacting the compound (II) or a salt thereof with the compound (XXXII) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvent which does not adversely affect the reaction. These conventional solvent may also be used in a mixture with water.

The reaction temperature is not critical and the reaction is usually carried out under warming to heating.

The reaction is usually carried out in the presence of an acid including Lewis acid.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, zinc halide (e.g. zinc chloride, zinc bromide, etc.), etc.] and the like.

When the acid and/or the starting compound are in liquid, they can be also used as a solvent.

Process (20)

The compound (Iz) or a salt thereof can be prepared by reacting the compound (II) or a salt thereof with the compound (XXXIII) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvent which does not adversely affect the reaction. These conventional solvent may also be used in a mixture with water.

The reaction temperature is not critical and the reaction is usually carried out under warming to heating.

The reaction is usually carried out in the presence of an acid including Lewis acid.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, zinc halide (e.g. zinc chloride, zinc bromide, etc.), etc.] and the like.

When the acid and/or the starting compound are in liquid, they can be also used as a solvent.

Process (21)

The compound (Ij) or a salt thereof can be prepared by reacting the compound (IIa) or a salt thereof with the compound (XXXIV) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvent which does not adversely affect the reaction. These conventional solvent may also be used in a mixture with water.

The reaction temperature is not critical and the reaction is usually carried out under warming to heating.

The reaction is usually carried out in the presence of an acid including Lewis acid.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, zinc halide (e.g. zinc chloride, zinc bromide, etc.), etc.] and the like.

When the acid and/or the starting compound are in liquid, they can be also used as a solvent.

Process (22)

The compound (Is) or a salt thereof can be prepared by reacting the compound (II) or a salt thereof with the compound (XXXV) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvent which does not adversely affect the reaction. These conventional solvent may also be used in a mixture with water.

The reaction temperature is not critical and the reaction is usually carried out under warming to heating.

The reaction is usually carried out in the presence of an acid including Lewis acid.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, zinc halide (e.g. zinc chloride, zinc bromide, etc.), etc.] and the like.

When the acid and/or the starting compound are in liquid, they can be also used as a solvent.

Process (A)

The compound (VII) or a salt thereof can be prepared by reacting the compound (V) or a salt thereof with the compound (VI) or a salt thereof.

This reaction can be carried out in the manner disclosed in Preparation 1 or similar manners thereto.

Process (B)

The compound (IX) or a salt thereof can be prepared by reacting the compound (VII) or a salt thereof with the compound (VIII) or a salt thereof.

This reaction can be carried out in the manner disclosed in Preparation 2 or similar manners thereto.

Process (C)

The compound (X) or a salt thereof can be prepared by subjecting the compound (IX) or a salt thereof to cleavage reaction of O—N bond.

This reaction can be carried out in the manner disclosed in Preparation 4 or similar manners thereto.

Process (D)-①

The compound (XI) or a salt thereof can be prepared by subjecting the compound (X) or a salt thereof to halogenation reaction.

This halogenation is usually carried out by using a conventional halogenating agent such as halogen (e.g., chlorine, bromine, etc.), phosphorus trihalide (e.g., phosphorus tribromide, phosphorus trichloride, etc.), phosphorus pentahalide, (e.g., phosphorus pentachloride, phosphorus pentabromide, etc.), phosphorus oxychloride (e.g., phosphoryl trichloride, phosphoryl monochloride, etc.), thionyl halide (e.g., thionyl chloride, thionyl bromide, etc.), oxalyl halide (e.g., oxalyl chloride, oxalyl bromide, etc.) and the like.

This reaction is usually carried out in a solvent such as water, alcohol (e.g., methanol, ethanol, isopropyl alcohol, etc.), benzene, dioxane, N,N-dimethylformamide, tetrahydrofuran, methylene chloride, ethylene dichloride, chloroform, diethyl ether or any other solvent which does not adversely affect the reaction.

The reaction temperature is not critical and the reaction is usually carried out under cooling to warming.

Process (D)-②

The compound (IIa) or a salt thereof can be prepared by reacting the compound (XI) or a salt thereof with the compound (XII) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, diethyl ether or any other solvent which does not adversely affect the reaction.

The reaction temperature is not critical and the reaction is usually carried out under warming to heating.

Process (E)

The compound (X) or a salt thereof can be prepared by reacting the compound (XXII) or a salt thereof with the compound (XXIII) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvent which does not adversely affect the reaction. These conventional solvent may also be used in a mixture with water.

The reaction temperature is not critical and the reaction is usually carried out under warming to heating.

The reaction is usually carried out in the presence of an inorganic or an organic base such as an alkali metal (e.g., sodium, potassium, etc.), an alkali metal hydroxide (e.g., sodium hydroxide, potassium hydroxide, etc.), an alkali metal hydrogencarbonate (e.g., sodium hydrogencarbonate, potassium hydrogencarbonate, etc.), alkali metal carbonate (e.g., sodium carbonate, potassium carbonate, etc.), tri(lower)alkylamine (e.g., trimethylamine, triethylamine, diisopropylethylamine, etc.), alkali metal hydride (e.g., sodium hydride, etc.), alkali metal (lower)alkoxide (e.g., sodium methoxide, sodium ethoxide, etc.), pyridine lutidine, picoline, dimethylaminopyridine, N-(lower)alkylmorpholine, N,N-di(lower)alkylbenzylamine, N,N-di(lower)alkylaniline or the like.

When the base and/or the starting compound are in liquid, they can be also as a solvent.

Process (F)

The compound (IIa) or a salt thereof can be prepared by reacting the compound (X) or a salt thereof with the compound (XII) or a salt thereof.

This reaction is usually carried out in a solvent such as benzene, N,N-dimethylformamide, tetrahydrofuran, toluene, methylene chloride, ethylene dichloride, chloroform, dioxane, diethyl ether or any other solvent which does not adversely affect the reaction.

The reaction temperature is not critical and the reaction is usually carried out under warming to heating.

The reaction is usually carried out in the presence of an acid including Lewis acid.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, zinc halide (e.g. zinc chloride, zing bromide, etc.), etc.] and the like.

When the acid and/or the starting compound are in liquid, they can be also as a solvent.

Process (G)

The compound (XIII) or a salt thereof can be prepared by reacting the compound (II) or a salt thereof with the compound (XXIV) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, diethyl ether or any other solvent which does not adversely affect the reaction.

The reaction temperature is not critical and the reaction is usually carried out under cooling to warming.

Process (H)

The compound (XV) or a salt thereof can be prepared by reacting the compound (XXV) or a salt thereof with the compound (XXVI) or a salt thereof.

This reaction is usually carried out in a solvent such as benzene, tetrahydrofuran, toluene, methylene chloride, ethylene dichloride, chloroform, diethyl ether or any other solvent which does not adversely affect the reaction.

The reaction temperature is not critical and the reaction is usually carried out under cooling to heating.

The reaction may be also carried out in the presence of a strong inorganic or a strong organic base such as an alkali metal (e.g., sodium, etc.), alkali metal hydride (e.g. sodium hydride, etc.) or the like.

When the base and/or the starting compound are in liquid, they can be also as a solvent.

Process (I)

The compound (XVI) or a salt thereof can be prepared by subjecting the compound (IIa) or a salt thereof to diazotization reaction.

The reaction is usually carried out by using a conventional diazotizing agent such as a combination of an alkali metal nitrite (e.g., sodium nitrite, etc.) and an inorganic acid (e.g., hydrochloric acid, hydrobromic acid, nitric acid, sulfuric acid, etc.), a combination of isopentyl nitrite and an organic acid (e.g., acetic acid, benzoic acid, etc.) and the like.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, diethyl ether or any other solvent which does not adversely affect the reaction.

The reaction temperature is not critical and the reaction is usually carried out under cooling.

Process (J)

The compound (XXVIIa) or a salt thereof can be prepared by reacting the compound (II) or a salt thereof with the compound (XVIII) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvent which does not adversely affect the reaction. These conventional solvent may also be used in a mixture with water.

The reaction temperature is not critical and the reaction is usually carried out under cooling to heating.

The reaction is usually carried out in the presence of an inorganic or an organic base such as an alkali metal (e.g. sodium, potassium, etc.), an alkali metal hydroxide (e.g., sodium hydroxide, potassium hydroxide, etc.), an alkali metal hydrogencarbonate (e.g., sodium hydrogencarbonate, potassium hydrogencarbonate, etc.), alkali metal carbonate (e.g., sodium carbonate, potassium carbonate, etc.), tri (lower)alkylamine (e.g., trimethylamine, triethylamine, diisopropylethylamine, etc.), alkali metal hydride (e.g., sodium hydride, etc.), alkali metal (lower)alkoxide (e.g., sodium methoxide, sodium ethoxide, etc.), pyridine, lutidine, picoline, dimethylaminopyridine, N-(lower) alkylmorpholine, N,N-di(lower)alkylbenzylamine, N,N-di (lower)alkylaniline or the like.

When the base and/or the starting compound are in liquid, they can be also as a solvent.

Suitable salts of the object and starting compounds in Process (1)–(22) and (A)–(J) can be referred to the ones as exemplified for the compound (I).

The new pyrazole derivatives (I) and a pharmaceutically acceptable salt thereof of the present invention possess a strong inhibitory activity on the production of Interleukin-1 (IL-1) and a strong inhibitory activity on the production of tumor necrosis factor (TNF), and therefore are useful as an inhibitor on the production of Interleukin-1 (IL-1) and an inhibitor on the production of tumor necrosis factor (TNF).

Accordingly, the new pyrazole derivatives (I) and a pharmaceutically acceptable salt thereof can be used for prophylactic and therapeutic treatment of IL-1 and TNF mediated diseases such as chronic inflammatory diseases (e.g. rheumatoid arthritis, osteoarthritis, etc.) osteoporosis, rejection by transplantation, asthma, endotoxin shock, specific autoimmune diseases [e.g. ankylosing spondylitis, autoimmune hematological disorders (e.g. hemolyticodo anaemia, aplastic anaemia, pure red cell anaemia, idiopathic thrombocytopenia, etc.), systemic lupus erythematosus, polychondritis, scleroderma, Wegener granulamotosis, dermatomyositis, chronic active hepatitis, myasthenia gravis, psoriasis, idiopathic sprue, autoimmune inflammatory bowel disease (e.g. ulcerative colitis, Crohn's disease, etc.), endocrine opthalmopathy, Grave's disease, sarcoidosis, multiple scleosis, primary billiary cirrhosis, juvenile diabetes (diabetes mellitus type I), Reiter's syndrome, non infection uveitis, autoimmune keratitis (e.g. keratoconjuntivitis sicca, vernal keratoconjunctivitis, etc.), interstitial lung fibrosis, psoriatic arthritis, glomerulonephritis {e.g. nephrotic syndrome (e.g. idiopathic nephrotic syndrome, minimal change nephropathy, etc.), etc.}, etc.], cancer cachexia, AIDS cachexia, and the like.

In order to show the utilities of the pyrazole derivatives (I) and a pharmaceutically acceptable salt thereof of the present invention, pharmacological test data of the representative compound of the pyrazole derivatives (I) are illustrated in the following.

The expression of "Example 2-(1)" in the following test means the compound prepared in Example 2-(1).

(a) Inhibitory activity on the production of Interleukin-1 (IL-1)

1. Test method

Purified human peripheral blood monocyte were stimulated with bacterial lipopolysaccharide (1 µg/$10^4$ cells) in the absence or presence of appropriately diluted test compound for 2 days at 37° C. in a humidified 5% $CO_2$ atmosphere. Culture supernatants were tested for IL-1 ELISA assay.

Test compound was dissolved in absolute DMSO (dimethyl sulfoxide) to achieve 10 mM stock solutions and was subsequently diluted in serum free RPMI1640.

IL-1 levels were quantified by a commercial ELISA kit (Ohtsuka assay, Japan) using a sandwich technique. The sensitivity levels for the detection of IL-1β were 20 pg/ml.

The inhibitory concentration that caused a 50% inhibition ($IC_{50}$) was calculated by regression analysis of the dose-response data.

2. Test result

| Test compound | $IC_{50}$(M) |
| --- | --- |
| Example 2-(1) | $3.8 \times 10^{-8}$ |

(b) Inhibitory activity on the production of tumor necrosis factor (TNF)

1. Test method

Purified human peripheral blood monocyte were stimulated with bacterial lipopolysaccharide (1 µg/$10^4$ cells) in the absence or presence of appropriately diluted test compound for 2 days at 37° C. in a humidified 5% $CO_2$ atmosphere. Culture supernatants were tested for TNF ELISA assay.

TNF levels were quantified by a commercial ELISA kit (Endogen, Inc. USA) using a sandwich technique. The sensitivity levels for the detection of TNF were 12 pg/ml.

The inhibitory concentration that caused a 50% inhibition ($IC_{50}$) was calculated by regression analysis of the dose-response data.

2. Test result

| Test compound | IC$_{50}$(M) |
|---|---|
| Example 2-(1) | $1.16 \times 10^{-7}$ |

For therapeutic administration, the object compounds (I) of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as granule, capsule, tablet, dragee or suppository, or in a liquid form such as solution, suspension or emulsion for injection, ingestion, eye drops, etc. If needed, there may be included in the above preparation auxiliary substance such as stabilizing agent, wetting or emulsifying agent, buffer or any other commonly used additives.

The effective ingredient may usually be administered with a unit dose of 0.001 mg/kg to 500 mg/kg, preferably 0.01 mg/kg to 10 mg/kg, 1 to 4 times a day. However, the above dosage may be increased or decreased according to age, weight and conditions of the patient or the administering method.

Preferred embodiments of the object compound (I) are as follows.

$R^1$ is aryl which may have 1 to 3 substituent(s) selected from the group consisting of lower alkyl, lower alkoxy, lower alkenyl, lower alkynyl, mono(or di or tri)halo (lower)alkyl, halogen, carboxy, protected carboxy, hydroxy, protected hydroxy, aryl, ar(lower)alkyl, carboxy(lower)alkyl, protected carboxy(lower)alkyl, amino, protected amino, di(lower)alkylamino, hydroxy (lower)alkyl, protected hydroxy(lower)alkyl, nitro, acyl, cyano, mercapto, lower alkylthio, lower alkylsulfinyl, lower alkylsulfonyl and imino [more preferably phenyl which may have 1 to 3 substituent(s) selected from the group consisting of lower alkyl, lower alkoxy, lower alkenyl, lower alkynyl, mono(or di or tri)halo(lower)alkyl, halogen, carboxy, protected carboxy, hydroxy, protected hydroxy, aryl, ar(lower) alkyl, carboxy(lower)alkyl, protected carboxy(lower) alkyl, amino, protected amino, di(lower)alkylamino, hydroxy(lower)alkyl, protected hydroxy(lower)alkyl, nitro, acyl, cyano, mercapto, lower alkylthio, lower alkylsulfinyl, lower alkylsulfonyl and imino; most preferably halophenyl, lower alkylthiophenyl, lower alkylsulfinylphenyl or lower alkylsulfonylphenyl], or unsaturated 3 to 8-membered heteromonocyclic group containing 1 to 4-nitrogen atom(s) which may have 1 to 3 suitable substituent(s) [more preferably unsaturated 5 to 6-membered heteromonocyclic group containing 1 to 2 nitrogen atom(s), most preferably pyridyl], $R^2$ is aryl which may have 1 to 3 substituent(s) selected from the group consisting of lower alkyl, lower alkoxy, lower alkenyl, lower alkynyl, mono(or di or tri)halo (lower)alkyl, halogen, carboxy, protected carboxy, hydroxy, protected hydroxy, aryl, ar(lower)alkyl, carboxy(lower)alkyl, protected carboxy(lower)alkyl, amino, protected amino, di(lower)alkylamino, hydroxy (lower)alkyl, protected hydroxy(lower)alkyl, nitro, acyl, cyano, mercapto, lower alkylthio, lower alkylsulfinyl, lower alkylsulfonyl and imino [more preferably phenyl which may have 1 to 3 substituent(s) selected from the group consisting of lower alkyl, lower alkoxy, lower alkenyl, lower alkynyl, mono(or di or tri)halo(lower)alkyl, halogen, carboxy, protected carboxy, hydroxy, protected hydroxy, aryl, ar(lower) alkyl, carboxy(lower)alkyl, protected carboxy(lower) alkyl, amino, protected amino, di(lower)alkylamino, hydroxy(lower)alkyl, protected hydroxy(lower)alkyl, nitro, acyl, cyano, mercapto, lower alkylthio, lower alkylsulfinyl, lower alkylsulfonyl and imino; most preferably halophenyl], or unsaturated 3 to 8-membered heteromonocyclic group containing 1 to 4-nitrogen atom(s) which may have 1 to 3 substituent(s) selected from the group consisting of lower alkyl, lower alkoxy, lower alkenyl, lower alkynyl, mono(or di or tri)halo(lower)alkyl, halogen, carboxy, protected carboxy, hydroxy, protected hydroxy, aryl, ar(lower)alkyl, carboxy(lower)alkyl, protected carboxy(lower)alkyl, amino, protected amino, di(lower)alkylamino, hydroxy (lower)alkyl, protected hydroxy(lower)alkyl, nitro, acyl, cyano, mercapto, lower alkylthio, lower alkylsulfinyl, lower alkylsulfonyl and imino [more preferably unsaturated 5 to 6-membered heteromonocyclic group containing 1 to 2 nitrogen atom(s) which may have 1 to 2 substituent(s) selected from the group consisting of lower alkyl, lower alkoxy, lower alkenyl, lower alkynyl, mono(or di or tri)halo(lower)alkyl, halogen, carboxy, protected carboxy, hydroxy, protected hydroxy, aryl, ar(lower)alkyl, carboxy(lower) alkyl, protected carboxy(lower)alkyl, amino, protected amino, di(lower)alkylamino, hydroxy(lower)alkyl, protected hydroxy(lower)alkyl, nitro, lower alkanoyl, cyano, mercapto, lower alkylthio, lower alkylsulfinyl, lower alkylsulfonyl and imino; most preferably pyridyl which may have halogen or lower alkyl, pyrimidinyl, or dihydropyridyl which may have lower alkanoyl and lower alkyl], Y is a bivalent radical selected from

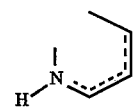

(in which ---- means single bond or double bond) which may have 1 to 6 (more preferably 1 to 3) substituent(s) selected from the group consisting of lower alkyl, lower alkoxy, lower alkenyl, lower alkynyl, mono(or di or tri)halo(lower)alkyl, halogen, carboxy, protected carboxy, hydroxy, protected hydroxy, aryl, ar(lower) alkyl, carboxy(lower)alkyl, protected carboxy(lower) alkyl, nitro, amino, protected amino, di(lower) alkylamino, hydroxy(lower)alkyl, protected hydroxy (lower)alkyl, acyl, cyano, mercapto, lower alkylthio, imino and oxo [more preferably

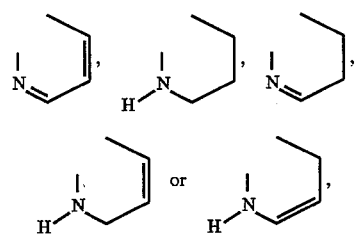

each of which may have 1 to 3 substituent(s) selected from the group consisting of phenyl, amino, acylamino, hydroxy, acyloxy, cyano, lower alkyl, lower alkanoyl, oxo, carboxy and lower alkoxycarbonyl; most preferably

which may have one or two substituent(s) selected from the group consisting of phenyl, amino, acylamino, hydroxy, acyloxy and cyano,

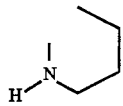

which may have one or two substituent(s) selected from the group consisting of lower alkyl, lower alkanoyl, lower alkoxycarbonyl and oxo,

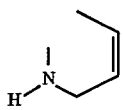

which may have oxo,

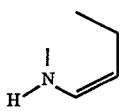

which may have one or two substituent(s) selected from the group consisting of lower alkyl, oxo, carboxy and protected carboxy, or

which may have 1 to 3 lower alkyl];

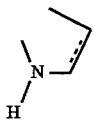

(in which ---- means single bond or double bond) which may have one or two substituent(s) selected from the group consisting of lower alkyl, lower alkoxy, lower alkenyl, lower alkynyl, mono(or di or tri)halo(lower) alkyl, halogen, carboxy, protected carboxy, hydroxy, protected hydroxy, aryl which may have suitable substituent(s), ar(lower)alkyl, carboxy(lower)alkyl, protected carboxy(lower)alkyl, nitro, amino, protected amino, di(lower)alkylamino, hydroxy(lower)alkyl, protected hydroxy(lower)alkyl, acyl, cyano, mercapto, lower alkylthio, imino and oxo [more preferably

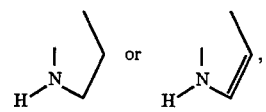

each of which may have one or two substituent(s) selected from the group consisting of oxo and phenyl which may have halogen];

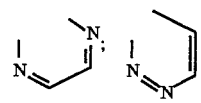

which may have one or two substituent(s) selected from the group consisting of lower alkyl, lower alkoxy, lower alkenyl, lower alkynyl, mono(or di or tri)halo (lower)alkyl, halogen, carboxy, protected carboxy, hydroxy, protected hydroxy, aryl, ar(lower)alkyl, carboxy(lower)alkyl, protected carboxy(lower)alkyl, nitro, amino, protected amino, di(lower)alkylamino, hydroxy(lower)alkyl, protected hydroxy(lower)alkyl, acyl, cyano, mercapto, lower alkylthio, imino and oxo [more preferably

which may have one or two substituent(s) selected from the group consisting of lower alkyl and phenyl] and

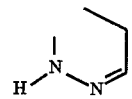

which may have 1 to 4 (more preferably one or two) substituent(s) selected from the group consisting of lower alkyl, lower alkoxy, lower alkenyl, lower alkynyl, mono(or di or tri)halo(lower)alkyl, halogen, carboxy, protected carboxy, hydroxy, protected hydroxy, aryl, ar(lower)alkyl, carboxy(lower)alkyl, protected carboxy(lower)alkyl, nitro, amino, protected amino, di(lower)alkylamino, hydroxy(lower)alkyl, protected hydroxy(lower)alkyl, acyl, cyano, mercapto, lower alkylthio, imino and oxo [more preferably

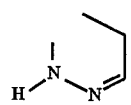

which may have lower alkyl].

The following Preparations and Examples are given for the purpose of illustrating the present invention in more detail.

Preparation 1

A mixture of 1-(4-fluorophenyl)-2-(pyridin-4-yl)ethan-1-one (5.12 g) and N,N-dimethylformamide dimethyl acetal (16 ml) was stirred at 100° C. for 3 hours under nitrogen. The cooled mixture was concentrated in vacuo. The residue was crystallized from isopropyl ether to yield 3-dimethylamino-1-(4-fluorophenyl)-2-(pyridin-4-yl)-2-propen-1-one (6.15 g).

NMR (CDCl$_3$, δ): 2.82 (6H, s), 6.99 (2H, t, J=9 Hz), 7.03 (2H, d, J=6 Hz), 7.35–7.55 (3H, m), 8.48 (2H, br)

Preparation 2

A mixture of 3-dimethylamino-1-(4-fluorophenyl)-2-(pyridin-4-yl)-2-propen-1-one (6.15 g) and hydroxylamine hydrochloride (4.75 g) in dry ethanol (40 ml) was refluxed for 20 minutes. The mixture was cooled and concentrated in vacuo. The residue was dissolved in dilute hydrochloric acid and then treated with an aqueous saturated sodium bicarbonate solution. The precipitates were collected by filtration, washed with water, and dried to give 5-(4-fluorophenyl)-4-(pyridin-4-yl)isoxazole (5.35 g).

mp: 95°–97° C.

NMR (CDCl$_3$, δ): 7.15 (2H, t, J=9 Hz), 7.37 (2H, d, J=6 Hz), 7.61 (2H, dd, J=5 Hz and 9 Hz), 8.46 (1H, s), 8.67 (2H, d, J=6 Hz)

Preparation 3

The following compound was obtained according to similar manners to those of Preparation 1 and Preparation 2.

5-(4-Fluorophenyl)-4-(pyrimidin-4-yl)isoxazole mp: 125°–126° C.

NMR (CDCl$_3$, δ): 7.22 (2H, t, J=9 Hz), 7.40 (1H, d, J=5 Hz), 7.83 (2H, dd, J=5 Hz and 9 Hz), 8.69 (1H, d, J=5 Hz), 8.80 (1H, s), 9.26 (1H, s)

Preparation 4

(1) A suspension of 5-(4-fluorophenyl)-4-(pyridin-4-yl)isoxazole (5.35 g) in 1N sodium hydroxide aqueous solution (50 ml) was stirred for one hour at 60° C. The solution was cooled and adjusted to pH 6 with concentrated hydrochloric acid. The separated solid was collected, washed with water, and dried to give 3-(4-fluorophenyl)-3-oxo-2-(pyridin-4-yl)propanenitrile (5.27 g).

mp: 222°–225° C.

NMR (CDCl$_3$+CD$_3$OD, δ): 7.11 (2H, t, J=9 Hz), 7.77 (2H, dd, J=5 Hz and 9 Hz), 7.82 (2H, d, J=6 Hz), 8.21 (2H, d, J=6 Hz)

The following compound was obtained according to a similar manner to that of Preparation 4-(1).

(2) 3-(4-Fluorophenyl)-3-oxo-2-(pyrimidin-4-yl)propanenitrile mp: 208°–210° C.

NMR (CDCl$_3$+CD$_3$OD, δ): 7.18 (2H, t, J=9 Hz), 7.42 (1H, d, J=6 Hz), 7.93 (2H, dd, J=5 Hz and 9 Hz), 8.45 (1H, d, J=6 Hz), 8.68 (1H, s)

Preparation 5

(1) A solution of 3-(4-fluorophenyl)-3-oxo-2-(pyridin-4-yl)propanenitrile (240 mg) in phosphoryl trichloride (3 ml) was stirred for 15 minutes at 100° C. and then evaporated under reduced pressure. To the residue was added toluene and concentrated in vacuo, and the residue was dissolved in ethanol (2 ml). To the mixture was added hydrazine monohydrate (150 mg). The mixture was refluxed for 3 hours, cooled, and poured into an aqueous saturated sodium bicarbonate solution. The separated oil was extracted with a mixture of ethanol and dichloromethane (2:8). The extract was washed with water, dried and concentrated in vacuo. The residue was crystallized from methanol to yield 5-amino-3-(4-fluorophenyl)-4-(pyridin-4-yl)pyrazole (110 mg).

mp: >250° C.

NMR (CDCl$_3$+CD$_3$OD, δ): 7.08 (2H, t, J=9 Hz), 7.23 (2H, d, J=6 Hz), 7.33 (2H, dd, J=5 Hz and 9 Hz), 8.42 (2H, d, J=6 Hz)

The following compound was obtained according to a similar manner to that of Preparation 5-(1).

(2) 5-Amino-3-(4-fluorophenyl)-4-(pyrimidin-4-yl)pyrazole mp: 240°–242° C.

NMR (CDCl$_3$+CD$_3$OD, δ): 6.81 (1H, d, J=5 Hz), 7.19 (2H, t, J=9 Hz), 7.48 (2H, dd, J=5 Hz and 9 Hz), 8.23 (1H, d, J=5 Hz), 8.99 (1H, s)

Preparation 6

The following compound was obtained according to a similar manner to that of Preparation 1.

3-Dimethylamino-1-(4-fluorophenyl)-2-(3-methylpyridin-4-yl)-2-propen-1-one mp: 80°–81° C.

NMR (CDCl$_3$, δ): 2.16 (3H, s), 2.19 (6H, s), 7.01 (2H, t, J=9 Hz), 7.10 (1H, d, J=6 Hz), 7.38 (1H, s), 7.49 (2H, dd, J=5 Hz, 9 Hz), 8.39 (1H, d, J=6 Hz), 8.41 (1H, s)

Preparation 7

The following compound was obtained according to a similar manner to that of Preparation 2.

5-(4-Fluorophenyl)-4-(3-methylpyridin-4-yl)isoxazole mp: 122°–124° C.

NMR (CDCl$_3$, δ): 2.18 (3H, s), 7.09 (2H, t, J=9 Hz), 7.26 (1H, d, J=6 Hz), 7.49 (2H, dd, J=5 Hz, 9 Hz), 8.30 (1H, s), 8.52 (1H, d, J=6 Hz), 8.61 (1H, s)

Preparation 8

The following compounds were obtained according to similar manners to those of Preparation 1 and Preparation 2.

(1) 5-(4-Methylthiophenyl)-4-(pyridin-4-yl)isoxazole mp: 108°–109° C.

NMR (CDCl$_3$, δ): 2.52 (3H, s), 7.27 (2H, d, J=9 Hz), 7.32 (2H, d, J=6 Hz), 7.53 (2H, d, J=9 Hz), 8.40 (1H, s), 8.64 (2H, d, J=6 Hz)

(2) 5-(4-Fluorophenyl)-4-(2-fluoropyridin-4-yl)isoxazole mp: 111°–112° C.

NMR (CDCl$_3$, δ): 6.95 (1H, s), 7.16 (2H, t, J=9 Hz), 7.19 (1H, d, J=6 Hz), 7.62 (2H, dd, J=5 Hz, 9 Hz), 8.27 (1H, d, J=6 Hz), 8.45 (1H, s)

(3) 5-(4-Fluorophenyl)-4-(pyridin-2-yl)isoxazole

NMR (CDCl$_3$, δ): 7.15 (2H, t, J=9 Hz), 7.27 (1H, t, J=7 Hz), 7.49 (1H, d, J=7 Hz), 7.69 (1H, t, J=7 Hz), 7.78 (2H, dd, J=5 Hz, 9 Hz), 8.67 (1H, s), 8.69 (1H, d, J=7 Hz)

Preparation 9

The following compounds were obtained according to a similar manner to that of Preparation 4-(1).

(1) 3-(4-Methylthiophenyl)-3-oxo-2-(pyridin-4-yl)propanenitrile mp: 234°–235° C.

NMR (CDCl$_3$+CD$_3$OD, δ): 2.49 (3H, s), 7.21 (2H, d, J=9 Hz), 7.62 (2H, d, J=9 Hz ), 7.80 (2H, d, J=6 Hz), 8.15 (2H, d, J=6 Hz)

(2) 3-(4-Fluorophenyl)-2-(2-fluoropyridin-4-yl)-3-oxopropanenitrile mp: 131°–136° C.

NMR (CDCl$_3$+CD$_3$OD, δ): 7.18 (2H, t, J=9 Hz ), 7.52–7.74 (4H, m), 8.00 (1H, d, J=6 Hz)

(3) 3-(4-Fluorophenyl)-2-(3-methylpyridin-4-yl)-3-oxopropanenitrile mp: 151°–153° C.

NMR (CDCl$_3$+CD$_3$OD, δ): 2.40 (3H, s), 7.08 (2H, t, J=9 Hz), 7.71 (2H, dd, J=5 Hz, 9 Hz ), 7.88 (1H, d, J=6 Hz), 7.90 (1H, s), 8.19 (1H, d, J=6 Hz)

(4) 3-(4-Fluorophenyl)-3-oxo-2-(pyridin-2-yl)propanenitrile mp: 203°–205° C.

NMR (CDCl$_3$, δ) 7.00–7.20 (3H, m), 7.62 (1H, d, J=8 Hz), 7.80–8.05 (4H, m)

Preparation 10

The following compounds were obtained according to a similar manner to that of Preparation 5-(1).

(1) 5-Amino-3-(4-fluorophenyl)-4-(2-fluoropyridin-4-yl)pyrazole mp: 237°–239° C.

NMR (CDCl₃+CD₃OD, δ): 6.89 (1H, br s), 7.03–7.18 (3H, m), 7.38 (2H, dd, J=5 Hz, 9 Hz), 8.05 (1H, d, J=6 Hz)

(2) 5-Amino-3-(4-fluorophenyl)-4-(3-methylpyridin-4-yl)pyrazole mp: >250° C.

NMR (CDCl₃+CD₃OD, δ): 2.00 (3H, s), 6.95 (2H, t, J=9 Hz), 7.10–7.30 (3H, m), 8.31 (1H, d, J=6 Hz), 8.39 (1H, s)

(3) 5-Amino-3-(4-fluorophenyl)-4-(pyridin-2-yl)pyrazole mp: 151°–152° C.

NMR (CDCl₃, δ): 6.60–7.15 (7H, m), 7.30–7.50 (3H, m), 8.53 (1H, d, J=5 Hz )

(4) 5-Amino-3-(4-fluorophenyl)-4-(pyridin-3-yl)pyrazole mp: 173°–176° C.

NMR (CDCl₃+CD₃OD, δ): 7.03 (2H, t, J=9 Hz), 7.20–7.40 (3H, m), 7.62 (1H, d, J=8 Hz), 8.40–8.50 (2H, m)

Preparation 11

(1) Sodium (2.48 g) was dissolved in dry ethanol (37 ml) under nitrogen atmosphere. To the solution was added 4-fluorophenylacetonitrile (11.65 g) and ethyl isonicotinate (16.41 ml) and the solution was refluxed for 3 hours. The reaction mixture was cooled and poured into water. The ethanol of the mixture was removed under reduced pressure. The resulting aqueous solution was washed with ether and neutralized with diluted hydrochloric acid. The separated solid was collected, washed with water and dried to give 2-(4-fluorophenyl)-3-oxo-3-(pyridin-4-yl)propanenitrile (16.43 g).

mp: 230°–232° C.

NMR (CDCl₃+CD₃OD, δ): 7.12 (2H, t, J=9 Hz), 7.68 (2H, d, J=6 Hz), 7.84 (2H, dd, J=5 Hz, 9 Hz), 8.69 (2H, d, J=6 Hz)

The following compound was obtained according to a similar manner to that of Preparation 11-(1).

(2) 3-(4-Fluorophenyl)-3-oxo-2-(pyridin-3-yl)propanenitrile mp: 240°–245° C.

NMR (DMSO-d₆, δ): 7.23 (2H, t, J=9 Hz), 7.60–7.80 (3H, m), 8.30 (1H, d, J=5 Hz), 8.48 (1H, d, J=8 Hz), 9.63 (1H, s)

Preparation 12

A mixture of 2-(4-fluorophenyl)-3-oxo-3-(pyridin-4-yl)propanenitrile (10 g), hydrazine monohydrate (2.4 ml) and acetic acid (5.2 ml) in dry benzene (100 ml) was refluxed for 4 hours. The reaction mixture was cooled and extracted with 3N-hydrochloric acid (80 ml×3). The extracts were concentrated in vacuo to 100 ml of the volume and the solution was neutralized with aqueous ammonia solution. The separated solid was collected, washed with water and dried to give 5-amino-4-(4-fluorophenyl)-3-(pyridin-4-yl)pyrazole (2.02 g).

mp: 116°–118° C.

NMR (CDCl₃+CD₃OD, δ): 7.12 (2H, t, J=9 Hz), 7.25 (2H, dd, J=5 Hz, 9 Hz), 7.38 (2H, d, J=6 Hz), 8.46 (2H, d, J=6 Hz)

Preparation 13

To a mixture of 3-(4-methylthiophenyl)-3-oxo-2-(pyridin-4-yl)propanenitrile (2.8 g) and N,N-dimethylformamide (0.42 ml) in dichloromethane (28 ml) was added oxalyl chloride (2.74 ml) dropwise under ice cooling. The mixture was stirred for 30 minutes at ambient temperature and the solution was concentrated in vacuo. The residue was dissolved in ethanol (28 ml) and to the solution was added hydrazine monohydrate (1.52 ml). The solution was refluxed for 2 hours and cooled. The separated solid was collected, washed with ethanol and dried to give 5-amino-3-(4-methylthiophenyl)-4-(pyridin-4-yl)pyrazole (1.576 g).

mp: >250° C.

NMR (DMSO-d₆, δ): 2.49 (3H, s), 4.60–4.90 (2H, br), 7.05–7.30 (6H, m), 8.41 (2H, d, J=6 Hz)

Preparation 14

To a solution of 4-methylpyridine (74.4 g) and ethyl 4-fluorobenzoate (134.4 g) in dry tetrahydrofuran (600 ml) was added a 1.0M solution of lithium bis(trimethylsilyl)amide in tetrahydrofuran (1.6 l) dropwise with ice cooling. The mixture was stirred at ambient temperature for 30 minutes. To the reaction mixture was added hexane (2.2 l) and the separated solid was collected, washed with hexane and dried. The obtained solid was dissolved in 3N-hydrochloric acid (800 ml) and the solution was neutralized with an aqueous saturated sodium bicarbonate solution. The separated solid was collected, washed with water and dried to give 1-(4-fluorophenyl)-2-(pyridin-4-yl)ethan-1-one (148 g).

mp: 93°–94° C.

NMR (CDCl₃, δ): 4.28 (2H, s), 7.09–7.25 (4H, m), 8.01 (1H, d, J=5 Hz), 8.06 (1H, d, J=5 Hz), 8.60 (2H, d, J=6 Hz)

EXAMPLE 1

(1) To a solution of 5-amino-3-(4-fluorophenyl)-4-(pyridin-4-yl)pyrazole (102 mg) in ethanol (3 ml) were added concentrated hydrochloric acid (50 μl), zinc chloride (27 mg) and 1,1,3,3-tetramethoxypropane (72 mg) in that order. The mixture was refluxed for one hour, cooled, and poured into an aqueous saturated sodium bicarbonate solution. The separated oil was extracted with dichloromethane. The extract was washed with brine, dried and concentrated in vacuo. The residue was crystallized from a mixture of ethyl acetate and diethyl ether to yield 2-(4-fluorophenyl)-3-(pyridin-4-yl)pyrazolo[1,5-a]pyrimidine (102 mg).

mp: 193.5°–194.5° C.

NMR (CDCl₃, δ): 6.97 (1H, dd, J=4 Hz and 7 Hz), 7.13 (2H, t, J=9 Hz), 7.54 (2H, d, J=6 Hz), 7.59 (2H, dd, J=5 Hz and 9 Hz), 8.50–8.70 (3H, m), 8.75 (1H, d, J=7 Hz)

The following compound was obtained according to a similar manner to that of Example 1-(1).

(2) 2-(4-Fluorophenyl)-3-(pyrimidin-4-yl)pyrazolo[1,5-a]pyrimidine mp: 240°–243° C.

NMR (CDCl₃+CD₃OD, δ): 7.09 (1H, dd, J=4 Hz and 6 Hz), 7.15 (2H, t, J=9 Hz), 7.68 (2H, dd, J=5 Hz and 9 Hz), 7.95 (1H, d, J=6 Hz), 8.65–8.80 (2H, m), 8.83 (1H, d, J=6 Hz), 9.14 (1H, s)

EXAMPLE 2

(1) A mixture of 2-(4-fluorophenyl)-3-(pyridin-4-yl)pyrazolo[1,5-a]pyrimidine (56 mg) and sodium borohydride (16 mg) in ethanol (2 ml) was refluxed for 2 hours, cooled, and poured into ice water. The separated oil was extracted with dichloromethane. The extract was washed with brine, dried and concentrated in vacuo. The residue was crystallized from a mixture of ethyl acetate and ethyl ether to yield 2-(4-fluorophenyl)-3-(pyridin-4-yl)-4,5,6,7-tetrahydropyrazolo[1,5-a]pyrimidine (44 mg).

mp: 207°–209° C.

NMR (CDCl₃, δ): 2.27 (2H, m), 3.40 (2H, m), 4.20 (2H, t, J=7 Hz), 4.50 (1H, s), 7.02 (2H, t, J=9 Hz), 7.08 (2H, d, J=6 Hz), 7.40 (2H, dd, J=5 Hz and 9 Hz), 8.46 (2H, d, J=6 Hz)

The following compound was obtained according to a similar manner to that of Example 2-(1).

(2) 2-(4-Fluorophenyl)-3-(pyrimidin-4-yl)-4,5,6,7-tetrahydropyrazolo[1,5-a]pyrimidine mp: 168°–169° C.

NMR (CDCl$_3$, δ): 2.26 (2H, m), 3.53 (2H, m), 4.18 (2H, t, J=7 Hz), 6.78 (1H, d, J=6 Hz), 7.14 (2H, t, J=9 Hz), 7.36 (1H, br s), 7.48 (2H, dd, J=5 Hz and 9 Hz), 8.22 (1H, br s), 8.94 (1H, s)

EXAMPLE 3

To a suspension of sodium hydride (288 mg) in N,N-dimethylformamide (20 ml) was added dropwise a solution of 5-amino-3-(4-fluorophenyl)-4-(pyridin-4-yl)pyrazole (1.524 g) in N,N-dimethylformamide (5 ml) with ice cooling. The mixture was stirred for 30 minutes and to the mixture was added a solution of ethyl chloroacetate (883 mg) in N,N-dimethylformamide (5 ml). After stirring of the mixture for 1 hour at ambient temperature, the reaction mixture was poured into water and the separated oil was extracted with dichloromethane. The extract was washed with brine, dried and concentrated in vacuo. The residue was dissolved in a solution of sodium (138 mg) in ethanol (5 ml) and the solution was refluxed for 1 hour. The reaction mixture was cooled, poured into water and neutralized with diluted hydrochloric acid. The separated oil was extracted with dichloromethane and the extract was washed with brine, dried and concentrated in vacuo. The residue was crystallized from ethanol to yield 2,3-dihydro-6-(4-fluorophenyl)-2-oxo-7-(pyridin-4-yl)-1H-imidazo[1,2-b]pyrazole (178 mg).

mp: >250° C.

NMR (CDCl$_3$+CD$_3$OD, δ): 4.70 (2H, s), 7.09 (2H, t, J=9.0 Hz), 7.12 (2H, d, J=6.0 Hz), 7.41 (2H, dd, J=5.0 Hz and 9 Hz), 8.40 (2H, d, J=6 Hz)

EXAMPLE 4

A mixture of 2,3-dihydro-6-(4-fluorophenyl)-2-oxo-7-(pyridin-4-yl)-1H-imidazo[1,2-b]pyrazole (50 mg) and diborane (0.34 mmol) in anhydrous tetrahydrofuran (5 ml) was refluxed under nitrogen atmosphere for 5 hours. After cooling of the reaction mixture, to the mixture was added 1N-hydrochloric acid (2 ml). The mixture was stirred at 60° C. for 30 minutes, cooled and neutralized with an aqueous saturated sodium bicarbonate solution. The separated oil was extracted with dichloromethane and the extract was washed with brine, dried and concentrated in vacuo. The residue was purified by thin layer chromatography on silica gel and the obtained crude solid was recrystallized from a mixture of diisopropyl ether and dichloromethane to yield 2,3-dihydro-6-(4-fluorophenyl)-7-(pyridin-4-yl)-1H-imidazo[1,2-b]pyrazole (14 mg).

mp: 213°–214° C.

NMR (CDCl$_3$+CD$_3$OD, δ): 4.05–4.19 (2H, m), 4.24–4.39 (2H, m), 7.02 (2H, d, J=6.0 Hz), 7.05 (2H, t, J=9.0 Hz), 7.46 (2H, dd, J=5.0 Hz and 9.0 Hz), 8.42 (2H, d, J=6.0 Hz)

EXAMPLE 5

To a suspension of 2-(4-fluorophenyl)-3-(pyridin-4-yl)-4,5,6,7-tetrahydropyrazolo[1,5-a]pyrimidine (100 mg) in methanol (2 ml) was added 10% methanolic hydrogen chloride (0.5 ml). The resulting clear solution was concentrated in vacuo. To the residue was added ethanol (3 ml) and the solution was concentrated in vacuo. The residue was crystallized from a mixture of ethanol and diethyl ether to give 2-(4-fluorophenyl)-3-(pyridin-4-yl)-4,5,6,7-tetrahydropyrazolo[1,5-a]pyrimidine dihydrochloride (100 mg).

mp: >250° C.

NMR (CD$_3$OD, δ): 2.30 (2H, m), 3.53 (2H, t, J=6 Hz), 4.28 (2H, t, J=6 Hz), 7.27 (2H, t, J=9 Hz), 7.51 (2H, dd, J=6 Hz, 9 Hz), 7.77 (2H, d, J=6 Hz), 8.65 (2H, d, J=6 Hz)

EXAMPLE 6

The following compounds were obtained according to a similar manner to that of Example 1-(1).

(1) 2-(4-Methylthiophenyl)-3-(pyridin-4-yl)pyrazolo-[1,5-a]pyrimidine mp: 182°–183° C.

NMR (CDCl$_3$, δ): 2.53 (3H, s), 6.98 (1H, dd, J=4 Hz, 7 Hz), 7.30 (2H, d, J=9 Hz), 7.55 (2H, d, J=9 Hz), 7.61 (2H, d, J=6 Hz), 8.58–8.67 (3H, m), 8.75 (1H, d, J=6 Hz)

(2) 2-(4-Fluorophenyl)-3-(2-fluoropyridin-4-yl)pyrazolo[1,5-a]pyrimidine mp: 175°–188° C. (dec.)

NMR (CDCl$_3$, δ): 6.97 (1H, dd, J=5 Hz, 7 Hz), 7.15 (2H, t, J=9 Hz), 7.27 (1H, s), 7.38 (1H, d, J=5 Hz), 7.59 (2H, dd, J=5 Hz, 9 Hz), 8.18 (1H, d, J=5 Hz), 8.62 (1H, d, J=5 Hz), 8.74 (1H, d, J=7 Hz)

(3) 2-(4-Fluorophenyl)-3-(3-methylpyridin-4-yl)pyrazolo-[1,5-a]pyrimidine mp: 174°–204° C. (dec.)

NMR (CDCl$_3$+CD$_3$OD, δ): 2.02 (3H, s), 6.88–7.10 (3H, m), 7.23 (1H, d, J=6 Hz), 7.30–7.58 (2H, m), 8.28–8.54 (3H, m), 8.78 (1H, d, J=6 Hz)

(4) 3-(4-Fluorophenyl)-2-(pyridin-4-yl)pyrazol[1,5-a]pyrimidine mp: 201°–202° C.

NMR (CDCl$_3$, δ): 6.95 (1H, dd, J=4 Hz, 8 Hz), 7.15 (2H, t, J=9 Hz), 7.47 (2H, dd, J=5 Hz, 9 Hz), 7.60 (2H, d, J=5 Hz), 8.58 (1H, d, J=4 Hz), 8.62 (2H, br), 8.74 (1H, d, J=8 Hz)

(5) 2-(4-Fluorophenyl)-3-(pyridin-2-yl)pyrazolo[1,5-a]pyrimidine mp: 189°–191° C.

NMR (CDCl$_3$, δ): 6.91 (1H, dd, J=4 Hz, 7 Hz), 7.08 (2H, t, J=9 Hz), 7.23 (1H, t, J=5 Hz), 7.55–7.80 (4H, m), 8.59 (1H, d, J=4 Hz), 8.65–8.80 (2H, m)

(6) 2-(4-Fluorophenyl)-3-(pyridin-3-yl)pyrazolo[1,5-a]pyrimidine mp: 154°–157° C.

NMR (CDCl$_3$, δ): 6.93 (1H, dd, J=4 Hz, 7 Hz), 7.10 (2H, t, J=9 Hz), 7.37 (1H, dd, J=5 Hz, 8 Hz), 7.61 (2H, dd, J=5 Hz, 9 Hz), 7.91 (1H, d, J=8 Hz), 8.55 (2H, d, J=4 Hz), 8.73 (1H, d, J=7 Hz), 8.76 (1H, s)

EXAMPLE 7

The following compounds were obtained according to a similar manner to that of Example 2-(1).

(1) 3-(4-Fluorophenyl)-2-(pyridin-4-yl)-4,5,6,7-tetrahydropyrazolo[1,5-a]pyrimidine mp: 241°–242° C.

NMR (CDCl$_3$+CD$_3$OD, δ): 2.27 (2H, m), 3.37 (2H, m), 4.23 (2H, t, J=6 Hz), 7.08 (2H, t, J=9 Hz), 7.20 (2H, dd, J=5 Hz, 9 Hz), 7.41 (2H, d, J=6 Hz), 8.48 (2H, d, J=6 Hz)

(2) 2-(4-Methylthiophenyl)-3-(pyridin-4-yl)-4,5,6,7-tetrahydropyrazolo[1,5-a]pyrimidine mp: 201°–202° C.

NMR (CDCl$_3$, δ): 2.18–2.31 (2H, m), 2.49 (3H, s), 3.32–3.44 (2H, m), 4.20 (2H, t, J=6 Hz), 4.42 (1H, br s), 7.09 (2H, d, J=6 Hz), 7.29 (2H, d, J=9 Hz), 7.38 (2H, d, J=9 Hz), 8.44 (2H, d, J=6 Hz)

(3) 2-(4-Fluorophenyl)-3-(2-fluoropyridin-4-yl)-4,5,6,7-tetrahydropyrazolo[1,5-a]pyrimidine mp: 181°–182° C.

NMR (CDCl$_3$, δ): 2.17–2.38 (2H, m), 3.34–3.49 (2H, m), 4.20 (2H, t, J=7 Hz), 4.48 (1H, br s), 6.79 (1H, s), 6.82–6.94 (1H, m), 7.02 (2H, t, J=9 Hz), 7.39 (2H, dd, J=5 Hz, 9 Hz), 8.03 (1H, d, J=6 Hz)

(4) 2-(4-Fluorophenyl)-3-(3-methylpyridin-4-yl)-4,5,6,7-tetrahydropyrazolo[1,5-a]pyrimidine mp: 213°–214° C.

NMR (CDCl$_3$, δ): 2.00 (3H, s), 2.16–2.35 (2H, m), 3.29–3.45 (2H, m), 4.09 (1H, br s), 4.22 (2H, t, J=7 Hz), 6.90 (2H, t, J=9 Hz), 7.10 (1H, d, J=6 Hz), 7.30 (2H, dd, J=5 Hz, 9 Hz), 8.35 (1H, d, J=6 Hz), 8.40 (1H, s)

(5) 2-(4-Fluorophenyl)-3-(2-methylpyridin-4-yl)-4,5,6,7-tetrahydropyrazolo[1,5-a]pyrimidine mp: 190°–191° C.

NMR (CDCl$_3$, δ): 2.19–2.35 (2H, m), 2.49 (3H, s), 3.33–3.47 (2H, m), 4.21 (2H, t, J=6 Hz), 4.39 (1H, br s), 6.85 (1H, d, J=6 Hz), 6.96 (1H, s), 7.00 (2H, t, J=9 Hz), 7.40 (2H, dd, J=5 Hz, 9 Hz), 8.35 (1H, d, J=6 Hz)

(6) 2-(4-Fluorophenyl)-3-(pyridin-2-yl)-4,5,6,7-tetrahydropyrazolo[1,5-a]pyrimidine mp : 170°–172° C.

NMR (CDCl$_3$, δ): 2.23 (2H, m), 3.48 (2H, t, J=6 Hz), 4.18 (2H, t, J=6 Hz), 6.85–6.95 (2H, m), 7.00–7.15 (3H, m), 7.37 (1H, t, J=7 Hz), 7.51 (2H, dd, J=5 Hz, 9 Hz), 8.46 (1H, d, J=5 Hz)

(7) 2-(4-Fluorophenyl)-3-(pyridin-3-yl)-4,5,6,7-tetrahydropyrazolo[1,5-a]pyrimidine mp: 115°–118° C.

NMR (CDCl$_3$, δ): 2.25 (2H, m), 3.37 (2H, t, J=6 Hz), 4.21 (2H, t, J=6 Hz), 4.35 (1H, s), 6.98 (2H, t, J=9 Hz), 7.22 (1H, dd, J=5 Hz, 7 Hz), 7.30–7.50 (3H, m), 8.40 (1H, d, J=5 Hz), 8.52 (1H, s)

EXAMPLE 8

The following compound was obtained according to a similar manner to that of Example 4.

2-(4-Fluorophenyl)-4-methyl-3-(pyridin-4-yl)-4,5,6,7-tetrahydropyrazolo[1,5-a]pyrimidine mp: 126°–128° C.

NMR (CDCl$_3$, δ): 2.14–2.38 (2H, m), 2.62 (3H, s), 3.21 (2H, t, J=6 Hz), 4.19 (2H, t, J=6 Hz), 6.97 (2H, t, J=9 Hz), 7.15–7.30 (4H, m), 8.49 (2H, d, J=6 Hz)

EXAMPLE 9

To a solution of 5-amino-4-(4-fluorophenyl)-3-(pyridin-4-yl)pyrazole (1.674 g) in ethanol (33 ml) was added O-mesitylsulfonylhydroxylamine (2.362 g). The mixture was stirred at ambient temperature for 30 minutes and to the mixture was added a solution of glyoxal in water (40%, 955 mg). The mixture was refluxed for 4 hours and cooled. The reaction mixture was poured into an aqueous saturated sodium bicarbonate solution and the separated oil was extracted with dichloromethane. The extract was washed with brine, dried and concentrated in vacuo. The residue was purified by column chromatography on silica gel and the obtained oil was crystallized from ethanol to give 8-(4-fluorophenyl)-7-(pyridin-4-yl)pyrazolo[1,5-b][1,2,4]triazine (63 mg).

mp: 177°–178.5° C.

NMR (CDCl$_3$, δ): 7.19 (2H, t, J=9 Hz), 7.55–7.70 (4H, m), 8.59 (1H, d, J=5 Hz), 8.68 (2H, br), 8.91 (1H, d, J=5 Hz)

EXAMPLE 10

A mixture of sodium (28 mg), ethyl acetate (0.12 ml) and ethyl formate (0.10 ml) in dry toluene (0.5 ml) was stirred at ambient temperature for 14 hours under nitrogen. To the mixture was added 5-amino-4-(4-fluorophenyl)-3-(pyridin-4-yl)pyrazole (150 mg) in dry ethanol (1.5 ml) and the mixture was refluxed for 7 hours. The reaction mixture was cooled and the separated solid was collected and dried. The solid was dissolved in water (15 ml) and the solution was washed with ether. The aqueous solution was neutralized with diluted hydrochloric acid. The separated solid was collected, washed with water and dried to give 4,5-dihydro-3-(4-fluorophenyl)-5-oxo-2-(pyridin-4-yl)pyrazolo[1,5-a]pyrimidine (62 mg).

mp: 298°–299° C.

NMR (CDCl$_3$+CD$_3$OD, δ): 5.83 (1H, d, J=7 Hz), 7.25–7.50 (6H, m), 7.82 (1H, d, J=7 Hz), 8.58 (2H, br)

EXAMPLE 11

(1) To a mixture of 5-amino-4-(4-fluorophenyl)-3-(pyridin-4-yl)pyrazole (100 mg) and concentrated hydrochloric acid (0.2 ml) in water (0.4 ml) was added sodium nitrite (28 mg) in water (0.12 ml) under ice cooling. The mixture was stirred for 30 minutes and to the mixture were added cold dichloromethane (5 ml), an aqueous saturated sodium bicarbonate (2 ml) solution and 1-(triphenylphosphoranylidene)-2-propanone (126 mg) in dichloromethane (2 ml). The mixture was stirred at 10° C. for 2 hours. The organic layer was separated, dried and concentrated in vacuo. The residue was purified by column chromatography on silica gel and the obtained oil was crystallized from diisopropyl ether to give 8-(4-fluorophenyl)-4-methyl-7-(pyridin-4-yl)pyrazolo[5,1-c][1,2,4]triazine (41 mg).

mp: 202.5°–204.0° C.

NMR (CDCl$_3$, δ): 2.91 (3H, s), 7.18 (2H, t, J=9 Hz), 7.62 (2H, dd, J=5 Hz, 9 Hz), 7.68 (2H, d, J=6 Hz), 8.70 (2H, d, J=6 Hz), 8.79 (1H, s)

The following compound was obtained according to a similar manner to that of Example 11-(1).

(2) 8-(4-Fluorophenyl)-4-phenyl-7-(pyridin-4-yl)pyrazolo[5,1-c][1,2,4]triazine mp: 275°–276.5° C.

NMR (CDCl$_3$, δ): 7.20 (2H, t, J=9 Hz), 7.60–7.75 (7H, m), 8.33 (2H, m), 8.68 (2H, d, J=6 Hz), 9.05 (1H, s)

EXAMPLE 12

A mixture of 5-amino-3-(4-fluorophenyl)-4-(pyridin-4-yl)pyrazole (1.016 g), methyl acrylate (10 ml), pyridine (20 ml) and water (5 ml) was refluxed for 8 hours. The mixture was cooled and concentrated in vacuo. The residue was dissolved in a mixture of acetic acid (10 ml) and concentrated hydrochloric acid (1.5 ml). The solution was refluxed for 2 hours, cooled and neutralized with an aqueous saturated sodium bicarbonate solution. The separated solid was collected, washed with water and dried to give 2-(4-fluorophenyl)-5-oxo-3-(pyridin-4-yl)-4,5,6,7-tetrahydropyrazolo[1,5-a]pyrimidine (750 mg).

mp: >250° C.

NMR (CDCl$_3$, δ): 3.00 (2H, t, J=7 Hz), 4.43 (2H, t, J=7 Hz), 7.01 (2H, t, J=9 Hz), 7.13 (2H, d, J=6 Hz), 7.33 (2H, dd, J=5 Hz, 9 Hz), 8.47 (2H, d, J=6 Hz)

EXAMPLE 13

To a suspension of sodium hydride (60% dispersion in mineral oil, 35 mg) in dry N,N-dimethylformamide (5 ml) was added a solution of 2-(4-fluorophenyl)-5-oxo-3-(pyridin-4-yl)-4,5,6,7-tetrahydropyrazolo[1,5-a]pyrimidine (250 mg) in dry N,N-dimethylformamide (3 ml) dropwise under ice cooling. The mixture was stirred for 30 minutes and to the mixture was added a solution of methyl iodide (125 mg) in dry N,N-dimethylformamide (2 ml). The mixture was stirred at ambient temperature for 2 hours and poured into water. The separated oil was extracted with dichloromethane and the solution was washed with brine, dried and concentrated in vacuo. The residue was purified by column chromatography on silica gel and the obtained crude solid was recrystallized from a mixture of dichloromethane and diisopropyl ether to give 2-(4-fluorophenyl)-4-methyl-5-oxo-3-(pyridin-4-yl)-4,5,6,7-tetrahydropyrazolo[1,5-a]pyrimidine (180 mg).

mp: 185°–186° C.

NMR (CDCl$_3$, δ): 2.90 (3H, s), 3.06 (2H, t, J=7 Hz), 4.45 (2H, t, J=7 Hz), 6.99 (2H, t, J=9 Hz), 7.13–7.38 (4H, m), 8.61 (2H, d, J=6 Hz)

EXAMPLE 14

To a solution of 2-(4-methylthiophenyl)-3-(pyridin-4-yl)-4,5,6,7-tetrahydropyrazolo[1,5-a]pyrimidine (190 mg) in dichloromethane (6 ml) was added m-chloroperbenzoic acid (127 mg) under ice cooling. The mixture was stirred at ambient temperature for 30 minutes and diluted with dichloromethane. The solution was washed with an aqueous saturated sodium thiosulfate solution, an aqueous saturated sodium bicarbonate solution and brine, dried and concentrated in vacuo. The residue was purified by column chromatography on silica gel and the obtained crude solid was recrystallized from a mixture of 2-propanol and ether to give 2-(4-methylsulfinylphenyl)-3-(pyridin-4-yl)-4,5,6,7-tetrahydropyrazolo[1,5-a]pyrimidine (168 mg).

mp: 201°–202° C.

NMR (CDCl$_3$, δ): 2.20–2.37 (2H, m), 2.75 (3H, s), 3.35–3.48 (2H, m), 4.22 (2H, t, J=6 Hz), 4.50 (1H, br s), 7.09 (2H, d, J=6 Hz), 7.61 (4H, s), 8.49 (2H, d, J=6 Hz)

EXAMPLE 15

To a solution of 2-(4-methylthiophenyl)-3-(pyridin-4-yl)-4,5,6,7-tetrahydropyrazolo[1,5-a]pyrimidine (190 mg) in dichloromethane (6 ml) was added m-chloroperbenzoic acid (318 mg) under ice cooling. The mixture was stirred at ambient temperature for 1 hour and diluted with dichloromethane. The solution was washed with an aqueous saturated sodium thiosulfate solution, an aqueous saturated sodium bicarbonate solution and brine, dried and concentrated in vacuo. The residue was purified by column chromatography on silica gel and the obtained crude solid was recrystallized from a mixture of 2-propanol and ether to give 2-(4-methylsulfonylphenyl)-3-(pyridin-4-yl)-4,5,6,7-tetrahydropyrazolo[1,5-a]pyrimidine (63 mg).

mp: 236°–237° C. (dec.)

NMR (CDCl$_3$, δ): 2.20–2.38 (2H, m), 3.07 (3H, s), 3.35–3.48 (2H, m), 4.22 (2H, t, J=6 Hz), 4.48 (1H, br s), 7.09 (2H, d, J=6 Hz), 7.65 (2H, d, J=9 Hz), 7.88 (2H, d, J=9 Hz), 8.51 (2H, d, J=6 Hz)

EXAMPLE 16

To a solution of 2-(4-fluorophenyl)-3-(pyridin-4-yl)pyrazolo[1,5-a]pyrimidine (480 mg) in dry tetrahydrofuran (15 ml) was added acetyl chloride (0.89 ml) dropwise under ice cooling. The mixture was stirred at ambient temperature for 1 hour and to the mixture was added a solution of methyl magnesium bromide in tetrahydrofuran (1 mole solution, 12.42 ml) under ice cooling. The mixture was stirred at ambient temperature for 2 hours and to the mixture was added an aqueous saturated sodium bicarbonate solution. The separated oil was extracted with dichloromethane and the solution was washed with brine, dried and concentrated in vacuo. The residue was purified by column chromatography on silica gel to give 3-(1-acetyl-1,2-dihydro-2-methylpyridin-4-yl)-2-(4-fluorophenyl)pyrazolo[1,5-a]pyrimidine (327 mg).

NMR (CDCl$_3$, δ): 1.26 (3H, d, J=7 Hz), 2.21 (3H, s), 5.24–5.40 (1H, m), 5.47 (1H, d, J=7 Hz), 5.82 (1H, d, J=6 Hz), 6.52 (1H, d, J=7 Hz), 6.86 (1H, dd, J=4 Hz, 7 Hz), 7.15 (2H, t, J=9 Hz), 7.78 (2H, dd, J=5 Hz, 9 Hz), 8.51 (1H, d, J=4 Hz), 8.67 (1H, d, J=7 Hz)

EXAMPLE 17

A mixture of 3-(1-acetyl-1,2-dihydro-2-methylpyridin-4-yl)-2-(4-fluorophenyl)pyrazolo[1,5-a]pyrimidine (315 mg) and sulfur (146 mg) in decaline (3 ml) was stirred at 190° C. for 2 hours. The reaction mixture was cooled and purified by column chromatography on silica gel to give 2-(4-fluorophenyl)-3-(2-methylpyridin-4-yl)pyrazolo[1,5-a]pyrimidine (135 mg) as crystals.

mp: 164°–166° C.

NMR (CDCl$_3$, δ): 2.59 (3H, s), 6.95 (1H, dd, J=4 Hz, 7 Hz), 7.11 (2H, t, J=9 Hz), 7.26 (1H, d, J=5 Hz), 7.42 (1H, s), 7.61 (2H, dd, J=5 Hz, 9 Hz), 8.48 (1H, d, J=5 Hz), 8.59 (1H, d, J=5 Hz), 8.73 (1H, d, J=7 Hz)

EXAMPLE 18

A mixture of 3-(4-fluorophenyl)-2-(pyridin-4-yl)-4,5,6,7-tetrahydropyrazolo[1,5-a]pyrimidine (100 mg), triethylamine (0.4 ml) and acetic anhydride (0.2 ml) in dry 1,2-dichloroethane (3 ml) was refluxed for 2 days. The reaction mixture was cooled and concentrated in vacuo. The residue was dissolved in dichloromethane and the solution was washed with an aqueous saturated sodium bicarbonate solution and brine, dried and concentrated in vacuo. The residue was purified by column chromatography on silica gel and the obtained oil was crystallized from diisopropyl ether to give 4-acetyl-3-(4-fluorophenyl)-2-(pyridin-4-yl)-4,5,6,7-tetrahydropyrazolo[1,5-a]pyrimidine (60 mg).

mp: 184°–185° C.

NMR (CDCl$_3$, δ): 1.60 (s), 2.28 (2H, m), 4.01 (2H, t, J=6 Hz), 4.36 (2H, t, J=6 Hz), 7.00–7.25 (4H, m), 7.33 (2H, d, J=5 Hz), 8.52 (2H, d, J=5 Hz)

EXAMPLE 19

A mixture of 8-(4-fluorophenyl)-4-methyl-7-(pyridin-4-yl)pyrazolo[5,1-c][1,2,4]triazine (53 mg) and sodium borohydride (13 mg) in ethanol (1 ml) was refluxed for 3 hours, cooled and poured into ice-water. The separated oil was extracted with dichloromethane. The extract was washed with brine, dried and concentrated in vacuo. The residue was purified by column chromatography on silica gel and the obtained oil was crystallized from diisopropyl ether to give 1,4-dihydro-8-(4-fluorophenyl)-4-methyl-7-(pyridin-4-yl)pyrazolo[5,1-c][1,2,4]triazine (13 mg).

mp: 203.5°–204.5° C.

NMR (CDCl₃, δ): 1.75 (3H, d, J=7 Hz), 5.02 (1H, dq, J=2 Hz, 7 Hz), 6.78 (1H, d, J=2 Hz), 7.11 (2H, t, J=9 Hz), 7.20 (2H, dd, J=5 Hz, 9 Hz), 7.40 (2H, d, J=6 Hz), 7.84 (1H, s), 8.50 (2H, d, J=6 Hz)

EXAMPLE 20

2-(4-Fluorophenyl)-3-(pyridin-4-yl)-4,5,6,7-tetrahydropyrazolo[1,5-a]pyrimidine dihydrochloride (183 mg) was dissolved in hot aqueous isopropyl alcohol solution 15.5 ml). The solution was cooled and the separated solid was collected, washed with isopropyl alcohol and dried to give 2-(4-fluorophenyl)-3-(pyridin-4-yl)-4,5,6,7-tetrahydropyrazolo[1,5-a]pyrimidine hydrochloride 182 mg).

mp: >250° C.

IR (Nujol): 3300, 2550, 2040, 1955, 1855, 1625 cm⁻¹

NMR (CDCl₃, δ): 2.11–2.31 (2H, m), 3.48–3.63 (2H, m), 4.16 (2H, t, J=7 Hz), 7.09 (2H, t, J=9 Hz), 7.37 (2H, dd, J=5 Hz, 9 Hz), 7.59 (2H, d, J=6 Hz), 8.05 (2H, d, J=6 Hz)

EXAMPLE 21

To a suspension of 2-(4-fluorophenyl)-3-(pyridin-4-yl)-4,5,6,7-tetrahydropyrazolo[1,5-a]pyrimidine (250 mg) in ethanol (3.5 ml) was added 1N hydrochloric acid (0.85 ml). The resulting clear solution was concentrated in vacuo. To the residue was added ethanol (1 ml) and the solution was concentrated in vacuo. The residue was crystallized from a mixture of methanol (0.5 ml) and ethyl acetate (3 ml) and recrystallized from an aqueous isopropyl alcohol solution to give 2-(4-fluorophenyl)-3-(pyridin-4-yl)-4,5,6,7-tetrahydropyrazolo[1,5-a]pyrimidine hydrochloride (233 mg).

mp: >250° C.

IR (Nujol): 3300, 2550, 2040, 1955, 1855, 1625 cm⁻¹

NMR (CDCl₃, δ): 2.11–2.31 (2H, m), 3.48–3.63 (2H, m), 4.16 (2H, t, J=7 Hz), 7.09 (2H, t, J=9 Hz), 7.37 (2H, dd, J=5 Hz, 9 Hz), 7.59 (2H, d, J=6 Hz), 8.05 (2H, d, J=6 Hz)

EXAMPLE 22

A mixture of 5-amino-3-(4-fluorophenyl)-4-(pyridin-4-yl)pyrazole (153 mg), dibenzoylmethane (162 mg) and conc. hydrochloric acid (0.1 ml) in ethanol (5 ml) was refluxed for 4 hours. The reaction mixture was cooled and poured into ice-water. The mixture was neutralized with an aqueous saturated sodium bicarbonate solution. The separated oil was extracted with dichloromethane and the extract was washed with brine, dried and concentrated in vacuo. The residue was purified by column chromatography on silica gel and the obtained oil was crystallized from methanol to give 5,7-diphenyl-2-(4-fluorophenyl)-3-(pyridin-4-yl)pyrazolo[1,5-a]pyrimidine (250 mg).

mp: 243°–245° C.

NMR (CDCl₃, δ): 7.12 (2H, t, J=9 Hz), 7.45–7.70 (11H, m), 8.10–8.25 (4H, m), 8.61 (2H, d, J=6 Hz)

EXAMPLE 23

A mixture of 5-amino-3-(4-fluorophenyl)-4-(pyridin-4-yl)pyrazole (254 mg) and 4-methyl-3-penten-2-one (5 ml) was refluxed for 5 hours. The reaction mixture was cooled and concentrated in vacuo. The residue was purified by column chromatography on silica gel and the obtained oil was crystallized from a mixture of ethyl acetate and hexane to give 6,7-dihydro-2-(4-fluorophenyl)-3-(pyridin-4-yl)-5,7,7-trimethylpyrazolo[1,5-a]pyrimidine (83 mg).

mp: 171°–173° C.

NMR (CDCl₃, δ): 1.56 (6H, s), 2.33 (3H, s), 2.69 (2H, s), 7.03 (2H, t, J=9 Hz), 7.32 (2H, d, J=6 Hz), 7.45 (2H, dd, J=6 Hz, 9 Hz), 8.51 (2H, d, J=6 Hz)

EXAMPLE 24

To a solution of sodium (51 mg) in dry ethanol (3 ml) was added 5-amino-3-(4-fluorophenyl)-4-(pyridin-4-yl)pyrazole (254 mg) and diethyl malonate (176 mg). The mixture was refluxed for 5 hours and cooled. To the reaction mixture were added 1N-hydrochloric acid (4 ml) and water (6 ml). The separated solid was collected, washed with water and dried to give 5,7-dihydroxy-2-(4-fluorophenyl)-3-(pyridin-4-yl)pyrazolo[1,5-a]pyrimidine (210 mg).

mp: >250° C.

NMR (CD₃OD: NaOD=20:1, δ) : 7.12 (2H, t, J=9 Hz), 7.45–7.60 (4H, m), 8.12 (2H, d, J=6 Hz)

EXAMPLE 25

A mixture of 5-amino-3-(4-fluorophenyl)-4-pyridin-4-yl)pyrazole (100 mg) and ethyl acetoacetate (61 mg) in acetic acid (1 ml) was stirred for 1 hour at 100° C. After cooling, the reaction mixture was diluted with ethanol to crystallize. The crude crystalline was collected and washed with ethanol to give 4,7-dihydro-2-(4-fluorophenyl)-5-methyl-7-oxo-3-(pyridin-4-yl)pyrazolo[1,5-a]pyrimidine (104 mg).

mp: >280° C.

NMR (DMSO-d₆, δ): 2.30 (3H, s), 5.75 (1H, s), 7.20 (2H, t, J=9 Hz), 7.30 (2H, d, J=6 Hz), 7.45 (2H, dd, J=6.9 Hz), 8.60 (2H, d, J=6 Hz)

EXAMPLE 26

A mixture of 5-amino-3-(4-fluorophenyl)-4-(pyridin-4-yl)pyrazole (100 mg) and 1,1-dicyano-2-ethoxyethylene (49 mg) in acetic acid (2 ml) was refluxed for 1 hour. The reaction mixture was concentrated in vacuo and the residue was crystallized from ethanol to give 7-amino-6-cyano-2-(4-fluorophenyl)-3-(pyridin-4-yl)pyrazolo[1,5-a]pyrimidine (77 mg).

mp: >280° C.

NMR (DMSO-d₆, δ): 7.35 (2H, t, J=9 Hz), 7.45 (2H, d, J=6 Hz), 7.65 (2H, dd, J=6.9 Hz), 8.50 (1H, s), 8.55 (2H, d, J=6 Hz), 9.20 (2H, br s)

EXAMPLE 27

A mixture of 5-amino-3-(4-fluorophenyl)-4-(pyridin-4-yl)pyrazole (100 mg), 1,2-bis-(4-fluorophenyl)-2-hydroxyethan-1-one (167 mg) and concentrated hydrochloric acid (1 ml) in ethanol was refluxed for 5 hours. The reaction mixture was concentrated in vacuo and the obtained crystalline was washed with hot ethanol to give 2,3,6-tris-(4-fluorophenyl)-7-(pyridin-4-yl)-1H-imidazo[1,2-b]pyrazole hydrochloride (50 mg).

mp: >260° C.

NMR (DMSO-d₆, δ): 7.25 (6H, m), 7.55–7.80 (8H, m), 8.55 (2H, d, J=6 Hz)

EXAMPLE 28

A mixture of 5-amino-3-(4-fluorophenyl)-4-(pyridin-4-yl)pyrazole (1.02 g) and 1,1-bis(ethoxycarbonyl)-2-ethoxyethylene (864 mg) in acetic acid (10 ml) was refluxed for 3 hours. After cooling, the crude crystalline was obtained and washed with ethanol to give 4,7-dihydro-6- ethoxycarbonyl-2-(4-fluorophenyl)-3-(pyridin-4-yl)-7-oxopyrazolo[1,5-a]pyrimidine (1.23 g).

mp: >250° C.

EXAMPLE 29

To a mixture of 4,7-dihydro-6-ethoxycarbonyl-2-(4-fluorophenyl)-3-(pyridin-4-yl)-7-oxopyrazolo[1,5-a]pyrimidine (100 mg) in tetrahydrofuran (4 ml) was added lithium borohydride (2 mole in tetrahydrofuran, 0.26 ml) at room temperature and the mixture was refluxed for 1 hour. After cooling, the reaction mixture was quenched with an aqueous saturated ammonium chloride solution and extracted with ethyl acetate. The extracts were washed with brine, dried and concentrated in vacuo. The residue was crystallized from ethanol to give 6-ethoxycarbonyl-2-(4-fluorophenyl)-7-oxo-3-(pyridin-4-yl)-4,5,6,7-tetrahydropyrazolo[1,5-a]pyrimidine (40 mg).

mp: >250° C. (dec.)

NMR (DMSO-$d_6$, δ): 1.20 (3H, t, J=7 Hz), 3.70–3.95 (2H, m), 4.15–4.30 (3H, m), 7.20–7.35 (4H, m), 7.45 (2H, dd, J=6,9 Hz), 8.00 (1H, br s), 8.40 (2H, d, J=6 Hz)

EXAMPLE 30

A mixture of 4,7-dihydro-6-ethoxycarbonyl-2-(4-fluorophenyl)-3-(pyridin-4-yl)-7-oxopyrazolo[1,5-a]pyrimidine (946 mg) in sulfuric acid (40% in water, 5 ml) was refluxed for 2 hours. After cooling, the pH of the reaction mixture was adjusted to 5 with an aqueous saturated sodium bicarbonate solution. The crude crystalline was obtained and washed with hot ethanol to give 4,7-dihydro-6-carboxy-2-(4-fluorophenyl)-3-(pyridin-4-yl)-7-oxopyrazolo[1,5-a]pyrimidine (275 mg).

mp: 215°–218° C.

NMR (DMSO-$d_6$, δ): 7.40 (2H, t, J=9 Hz), 7.65 (2H, dd, J=6,9 Hz), 8.10 (2H, d, J=6 Hz), 8.60–8.70 (3H, m)

EXAMPLE 31

The following compounds were obtained according to a similar manner to that of Example 11-(1).

(1) 8-(4-Fluorophenyl)-7-(pyridin-4-yl)pyrazolo[5,1-c][1,2,4]triazine mp: 180°–182° C.

NMR (CDCl$_3$, δ): 7.20 (2H, t, J=9 Hz), 7.55–7.70 (4H, m), 8.59 (1H, d, J=5 Hz ), 8.70 (2H, d, J=6 Hz), 8.90 (1H, d, J=5 Hz)

(2) 7-(4-Fluorophenyl)-4-methyl-8-(pyridin-4-yl)pyrazolo[5,1-c][1,2,4]triazine mp: 220°–223° C. (dec.)

NMR (CDCl$_3$, δ): 2.90 (3H, s), 7.17 (2H, t, J=9 Hz), 7.60–7.75 (4H, m), 8.67 (2H, d, J=6 Hz), 8.81 (1H, s)

(3) 7-(4-Fluorophenyl)-8-(pyridin-4-yl)pyrazolo[5,1-c][1,2,4]triazine

NMR (CDCl$_3$, δ): 7.18 (2H, t, J=9 Hz), 7.60–7.75 (4H, m), 8.59 (1H, d, J=4 Hz), 8.68 (2H, d, J=6 Hz), 8.93 (1H, d, J=4 Hz)

EXAMPLE 32

To a solution of sodium (23 mg) in dry ethanol (3 ml) was added 5-amino-3-(4-fluorophenyl)-4-(pyridin-4-yl)pyrazole (254 mg) and ethyl cyanoacetate (113 mg). The mixture was refluxed for 5 hours and cooled. To the reaction mixture were added 1N-hydrochloric acid (2 ml) and water (5 ml). The separated solid was collected, washed with water and dried to give 7-amino-2-(4-fluorophenyl)-5-hydroxy-3-(pyridin-4-yl)pyrazolo[1,5-a]pyrimidine (270 mg).

mp: >250° C.

NMR (CD$_3$OD, δ): 5.69 (1H, s), 7.23 (2H, t, J=9 Hz), 7.56 (2H, dd, J=6 Hz, 9 Hz), 8.10 (2H, d, J=6 Hz), 8.40 (2H, d, J=6 Hz)

EXAMPLE 33

The following compound was obtained according to a similar manner to that of Example 18.

4-Acetyl-2-(4-fluorophenyl)-3-(pyridin-4-yl)-4,5,6,7-tetrahydropyrazolo[1,5-a]pyrimidine mp: 160°–161° C.

NMR (CDCl$_3$, δ): 1.66 (3H, s), 2.28 (2H, quint, J=6 Hz), 4.05 (2H, t, J=6 Hz), 4.33 (2H, t, J=6 Hz), 7.02 (2H, t, J=9 Hz), 7.10 (2H, d, J=6 Hz), 7.33 (2H, dd, J=6 Hz, 9 Hz), 8.57 (2H, d, J=6 Hz)

EXAMPLE 34

The following compounds were obtained according to a similar manner to that of Example 19.

(1) 1,4-Dihydro-7-(4-fluorophenyl)-4-methyl-8-(pyridin-4-yl)pyrazolo[5,1-c][1,2,4]triazine mp: 249°–251° C.

NMR (CDCl$_3$: CD$_3$OD=9:1, δ): 1.72 (3H, d, J=7 Hz), 5.01 (1H, dq, J=3 Hz, 7 Hz), 6.80 (1H, d, J=3 Hz), 7.06 (2H, t, J=9 Hz), 7.13 (2H, d, J=6 Hz), 7.42 (2H, dd, J=6 Hz, 9 Hz), 8.43 (2H, d, J=6 Hz)

(2) 1,4-Dihydro-8-(4-fluorophenyl)-7-(pyridin-4-yl)pyrazolo[5,1-c][1,2,4]triazine mp: >250° C.

NMR (CDCl$_3$: CD$_3$OD=9:1, δ): 4.88 (2H, d, J=3 Hz), 6.92 (1H, t, J=3 Hz), 7.11 (2H, t, J=9 Hz), 7.22 (2H, dd, J=6 Hz, 9 Hz), 7.38 (2H, d, J=6 Hz), 8.43 (2H, d, J=6 Hz)

(3) 1,4-Dihydro-7-(4-fluorophenyl)-8-(pyridin-4-yl)pyrazolo[5,1-c][1,2,4]triazine mp: 229°–232° C.

NMR (CDCl$_3$: CD$_3$OD=9:1, δ): 4.34 (2H, d, J=2 Hz), 6.96 (1H, t, J=2 Hz), 7.04 (2H, t, J=9 Hz), 7.13 (2H, d, J=6 Hz), 7.39 (2H, dd, J=6 Hz, 9 Hz), 8.45 (2H, d, J=6 Hz)

What we claim is:

1. A compound of the formula:

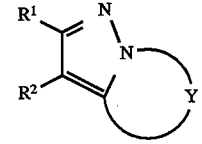

wherein $R^1$ is aryl, optionally substituted, or 5 to 6-membered heteromonocyclic group, optionally substituted, $R^2$ is aryl, optionally substituted, or 5 to 6-membered heteromonocyclic group, optionally substituted, and Y is a bivalent radical selected from

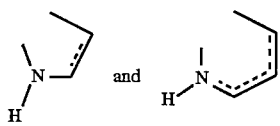 and in which ---- means single bond or double bond, optionally substituted, with the proviso that when Y is a bivalent radical

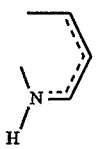

in which ---- means single bond or double bond, optionally substituted, then $R^2$ is aryl, optionally substituted, and pharmaceutically acceptable salts thereof.

2. A compound of claim 1, wherein $R^1$ is aryl, optionally having 1 to 3 substituent(s) selected from the group consisting of lower alkyl, lower alkoxy, lower alkenyl, lower alkynyl, mono(or di or tri)halo(lower)alkyl, halogen, carboxy, protected carboxy, hydroxy, protected hydroxy, aryl, ar(lower)alkyl, carboxy(lower)alkyl, protected carboxy (lower)alkyl, amino, protected amino, di(lower)alkylamino, hydroxy(lower)alkyl, protected hydroxy(lower)alkyl, nitro, acyl, cyano, mercapto, lower alkylthio, lower alkylsulfinyl, lower alkylsulfonyl and imino, or unsaturated 5 to 6-membered heteromonocyclic group containing 1 to 4-nitrogen atom(s) optionally having 1 to 3 substituent(s), $R^2$ is aryl, optionally having 1 to 3 substituent(s) selected from the group consisting of lower alkyl, lower alkoxy, lower alkenyl, lower alkynyl, mono(or di or tri)halo (lower) alkyl, halogen, carboxy, protected carboxy, hydroxy, protected hydroxy, aryl, ar(lower)alkyl, carboxy(lower)alkyl, protected carboxy(lower)alkyl, amino, protected amino, di(lower)alkylamino, hydroxy (lower)alkyl, protected hydroxy(lower)alkyl, nitro, acyl, cyano, mercapto, lower alkylthio, lower alkylsulfinyl, lower alkylsulfonyl and imino, or unsaturated 5 to 6-membered heteromonocyclic group containing 1 to 4-nitrogen atom(s) optionally having 1 to 3 substituent (s) selected from the group consisting of lower alkyl, lower alkoxy, lower alkenyl, lower alkynyl, mono(or di or tri)halo(lower) alkyl, halogen, carboxy, protected carboxy, hydroxy, protected hydroxy, aryl, ar(lower)alkyl, carboxy(lower)alkyl, protected carboxy(lower)alkyl, amino, protected amino, di(lower)alkylamino, hydroxy(lower)alkyl, protected hydroxy(lower)alkyl, nitro, acyl, cyano, mercapto, lower alkylthio, lower alkylsulfinyl, lower alkylsulfonyl and imino, Y is a bivalent radical selected from

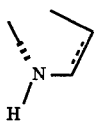

(in which ---- means single bond or double bond) optionally having one or two substituent(s) selected from the group consisting of lower alkyl, lower alkoxy, lower alkenyl, lower alkynyl, mono(or di or tri)halo (lower) alkyl, halogen, carboxy, protected carboxy, hydroxy, protected hydroxy, aryl optionally substituted, ar(lower)alkyl, carboxy(lower)alkyl, protected carboxy (lower)alkyl, nitro, amino, protected amino, di(lower) alkylamino, hydroxy(lower)alkyl, protected hydroxy (lower)alkyl, acyl, cyano, mercapto, lower alkylthio, imino and oxo; and

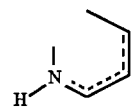

(in which ---- means single bond or double bond) optionally having 1 to 6 substituent(s) selected from the group consisting of lower alkyl, lower alkoxy, lower alkenyl, lower alkynyl, mono(or di or tri)halo(lower) alkyl, halogen, carboxy, protected carboxy, hydroxy, protected hydroxy, aryl, ar(lower)alkyl, carboxy(lower) alkyl, protected carboxy(lower)alkyl, nitro, amino, protected amino, di(lower)alkylamino, hydroxy(lower) alkyl, protected hydroxy(lower)alkyl, acyl, cyano, mercapto, lower alkylthio, imino and oxo; With the proviso that when is a bivalent radical selected from

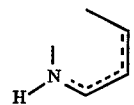

(in which ----- means single bond or double bond) optionally having 1 to 6 substituent(s) selected from the group consisting of lower alkyl, lower alkoxy, lower alkenyl, lower alkynyl, mono(or di or tri)halo(lower) alkyl, halogen, carboxy, protected carboxy, hydroxy, protected hydroxy, aryl, ar(lower)alkyl, carboxy(lower) alkyl, protected carboxy(lower)alkyl, nitro, amino, protected amino, di(lower)alkylamino, hydroxy(lower) alkyl, protected hydroxy(lower)alkyl, acyl, cyano, mercapto, lower alkylthio, imino and oxo; then $R^2$ is aryl, optionally having 1 to 3 substituent(s) selected from the group consisting of lower alkyl, lower alkoxy, lower alkenyl, lower alkynyl, mono(or di or tri)halo (lower) alkyl, halogen, carboxy, protected carboxy, hydroxy, protected hydroxy, aryl, ar(lower)alkyl, carboxy(lower)alkyl, protected carboxy(lower)alkyl, amino, protected amino, di(lower)alkylamino, hydroxy (lower)alkyl, protected hydroxy(lower)alkyl, nitro, acyl, cyano, mercapto, lower alkylthio, lower alkylsulfinyl, lower alkylsulfonyl and imino.

3. A compound of claim 2, wherein $R^1$ is phenyl optionally having 1 to 3 substituent(s) selected from the group consisting of lower alkyl, lower alkoxy, lower alkenyl, lower alkynyl, mono(or di or tri)halo(lower) alkyl, halogen, carboxy, protected carboxy, hydroxy, protected hydroxy, aryl, ar(lower) alkyl, carboxy(lower)alkyl, protected carboxy(lower) alkyl, amino, protected amino, di(lower)alkylamino, hydroxy(lower)alkyl, protected hydroxy(lower)alkyl, nitro, acyl, cyano, mercapto, lower alkylthio, lower alkylsulfinyl, lower alkylsulfonyl and imino, or unsaturated 5 to 6-membered heteromonocyclic group containing 1 to 2 nitrogen atom(s), $R^2$ is phenyl optionally having 1 to 3 substituent(s) selected from the group consisting of lower alkyl, lower alkoxy, lower alkenyl, lower alkynyl, mono(or di or tri)halo(lower)alkyl, halogen, carboxy, protected carboxy, hydroxy, protected hydroxy, aryl, ar(lower) alkyl, carboxy(lower)alkyl, protected carboxy(lower) alkyl, amino, protected amino, di(lower)alkylamino, hydroxy(lower)alkyl, protected hydroxy(lower)alkyl, nitro, acyl, cyano, mercapto, lower alkylthio, lower alkylsulfinyl, lower alkylsulfonyl and imino, or unsaturated 5 to 6-membered heteromonocyclic group containing 1 to 2 nitrogen atom(s) optionally having 1 to 2 substituent(s) selected from the group consisting of lower alkyl, lower alkoxy, lower alkenyl, lower alkynyl, mono(or di or tri)halo(lower)alkyl, halogen, carboxy, protected carboxy, hydroxy, protected hydroxy, aryl, ar(lower)alkyl, carboxy(lower)alkyl, protected carboxy(lower)alkyl, amino, protected amino, di(lower)alkylamino, hydroxy(lower)alkyl, protected hydroxy(lower)alkyl, nitro, lower alkanoyl, cyano, mercapto, lower alkylthio, lower alkylsulfinyl, lower alkylsulfonyl and imino, Y is a bivalent radical selected from

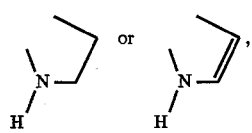

optionally having one or two substituent(s) selected from the group consisting of oxo and phenyl optionally having halogen, and

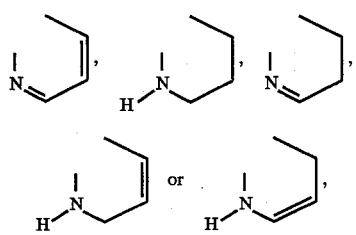

optionally having 1 to 3 substituent(s) selected from the group consisting of phenyl, amino, acylamino, hydroxy, acyloxy, cyano, lower alkyl, lower alkanoyl, oxo, carboxy and lower alkoxycarbonyl; with the proviso that when Y is a bivalent radical selected from

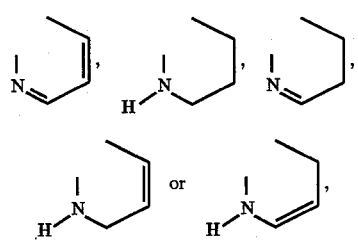

optionally having 1 to 3 substituent(s) selected from the group consisting of phenyl, amino, acylamino, hydroxy, acyloxy, cyano, lower alkyl, lower alkanoyl, oxo, carboxy and lower alkoxycarbonyl; then $R^2$ is phenyl optionally having 1 to 3 substituent(s) selected from the group consisting of lower alkyl, lower alkoxy, lower alkenyl, lower alkynyl, mono(or di or tri)halo(lower)alkyl, halogen, carboxy, protected carboxy, hydroxy, protected hydroxy, aryl, ar(lower) alkyl, carboxy(lower)alkyl, protected carboxy(lower) alkyl, amino, protected amino, di((lower)alkylamino, hydroxy(lower)alkyl, nitro, acyl, cyano, mercapto, lower alkylthio, lower alkylsulfinyl, lower alkylsulfonyl and imino.

4. A compound of claim 3, wherein $R^1$ is halophenyl, lower alkylthiophenyl, lower alkylsulfinylphenyl, lower alkylsulfonylphenyl or pyridyl, $R^2$ is halophenyl, pyridyl, optionally substituted by halogen or lower alkyl, pyrimidinyl, or dihydropyridyl optionally substituted by lower alkanoyl or lower alkyl, Y is a bivalent radical selected from

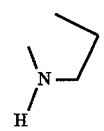

optionally having oxo group;

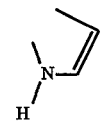

optionally substituted by one or two phenyl optionally having halogen;

optionally having one or two substituent(s) selected from the group consisting of phenyl, amino, acylamino, hydroxy, acyloxy and cyano;

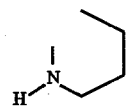

optionally having one or two substituent(s) selected from the group consisting of lower alkyl, lower alkanoyl, lower alkoxycarbonyl and oxo;

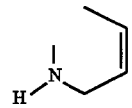

optionally having oxo;

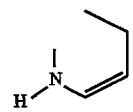

optionally having one or two substituent(s) selected from the group consisting of lower alkyl, oxo, carboxy and protected carboxy; and

optionally having 1 to 3 lower alkyl; with the proviso that when

optionally having one or two substituent(s) selected from the group consisting of phenyl, amino, acylamino, hydroxy, acyloxy and cyano;

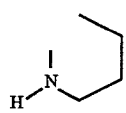

optionally having one or two substituent(s) selected from the group consisting of lower alkyl, lower alkanoyl, lower aklkoxycarbonyl and oxo;

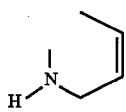

optionally having oxo;

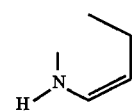

optionally having one or two substituent(s) selected from the group consisting of lower alkyl, oxo, carboxy and protected carboxy;

optionally having 1 to 3 lower alkyl; then $R^2$ is halophenyl.

5. A pharmaceutical composition which comprises, as an active ingredient, an effective amount of a compound of claim 1 or a pharmaceutically acceptable salt thereof in dmixture with pharmaceutically acceptable carriers.

6. A method for the prophylactic or therapeutic treatment of Interleukin-1 (IL-1) and tumor necrosis factor (TNF) mediated diseases which comprises administering an effective amount of a compound of claim 1 or a pharmaceutically acceptable salt thereof to a human or animal.

* * * * *

UNITED STATES PATENT AND TRADEMARK OFFICE
CERTIFICATE OF CORRECTION

PATENT NO. : 5,624,931
DATED : April 29, 1997
INVENTOR(S) : Teruo OKU, et al.

It is certified that error appears in the above-indentified patent and that said Letters Patent is hereby corrected as shown below:

On the title page, in Item [75], the sixth inventor's name and place of residence are missing. It should read:

--Hirokazu Tanaka          Tsuchiura, Japan--

Signed and Sealed this

Seventh Day of April, 1998

*Attest:*

BRUCE LEHMAN

*Attesting Officer*          *Commissioner of Patents and Trademarks*